(12) United States Patent
Shariat et al.

(10) Patent No.: US 11,911,095 B2
(45) Date of Patent: Feb. 27, 2024

(54) SEQUENTIAL MAPPING OF CARDIAC ARRHYTHMIA WITHOUT FIDUCIAL TIME REFERENCE

(71) Applicants: Queen's University at Kingston, Kingston (CA); Kingston Health Sciences Centre, Kingston (CA)

(72) Inventors: Mohammad Hassan Shariat, Kingston (CA); Damian P. Redfearn, Kingston (CA)

(73) Assignees: Queen's University at Kingston, Kingston (CA); Kingston Health Sciences Centre, Kingston (CA)

( * ) Notice: Subject to any disclaimer, the term of this patent is extended or adjusted under 35 U.S.C. 154(b) by 484 days.

(21) Appl. No.: 17/032,996

(22) Filed: Sep. 25, 2020

(65) Prior Publication Data

US 2021/0093217 A1 Apr. 1, 2021

Related U.S. Application Data

(60) Provisional application No. 62/907,072, filed on Sep. 27, 2019.

(51) Int. Cl.
*A61B 18/14* (2006.01)
*A61N 1/362* (2006.01)
(Continued)

(52) U.S. Cl.
CPC .......... *A61B 18/1492* (2013.01); *A61B 5/287* (2021.01); *A61B 5/333* (2021.01);
(Continued)

(58) Field of Classification Search
None
See application file for complete search history.

(56) References Cited

U.S. PATENT DOCUMENTS

2021/0000369 A1\* 1/2021 Luksic .................. A61B 34/20

FOREIGN PATENT DOCUMENTS

EP 3785609 A1 \* 3/2021 ......... A61B 18/1492

OTHER PUBLICATIONS

Masé, M. et al., "Automatic Reconstruction of Activation and Velocity maps from Electro-Anatomic data by Radial Basis"IEEE International Conference of the Engineering in Medicine and Biology Society (EMBO), pp. 2608-2611, (2010).
(Continued)

*Primary Examiner* — Kennedy Schaetzle
(74) *Attorney, Agent, or Firm* — Stephen J. Scribner

(57) ABSTRACT

A method for generating a propagation and velocity maps for cardiac wavefront propagation including cardiac arrhythmia, sinus rhythm, and paced rhythm. Activation time information is generated in the absence of any time alignment reference, wherein an estimated activation time is a weighted summation of potentially nonlinear and nonorthogonal candidate functions (CFs) selected from a bank of CFs. Time alignments between sequential recordings may be done by including binary level functions among selected CFs. Embodiments are applicable to single catheter mapping and sequential mapping, and are robust as confirmed by the ability to generate propagation maps and conduction velocity in the presence of multiple colliding wavefronts. The propagation and conduction velocity maps may be used for one or more of diagnosing cardiac arrhythmia, localizing cardiac arrhythmia, guiding catheter ablation therapy of cardiac arrhythmia, and guiding cardiac pacing therapy.

18 Claims, 15 Drawing Sheets

(51) Int. Cl.
 A61B 5/364 (2021.01)
 A61B 5/287 (2021.01)
 A61B 5/333 (2021.01)
 A61B 5/339 (2021.01)
 A61B 5/361 (2021.01)
 A61B 18/00 (2006.01)
(52) U.S. Cl.
 CPC ............. *A61B 5/339* (2021.01); *A61B 5/361* (2021.01); *A61B 5/364* (2021.01); *A61N 1/362* (2013.01); *A61B 2018/00351* (2013.01); *A61B 2018/00577* (2013.01)

(56) References Cited

OTHER PUBLICATIONS

Bayley, P.V., et al., "Estimation of Conduction Velocity Vector Fields from Epicardial Mapping Data", IEEE Transactions on Biomedical Engineering, vol. 45, No. 5, pp. 563-571, (1998).
Barnette, A.R., et al., "Estimation of 3-D Conduction Velocity Vector Fields from Cardiac Mapping Data", IEEE Biomedical Engineering, vol. 47, No. 8, pp. 1027-1035, (2000).
Dubois, R. et al., "Global and Directional Activation Maps for Cardiac Mapping in Electrophysiology", Computing in Cardiology, vol. 39, pp. 349-352, (2012).
Kojodjojo, P. et al., "Age-Related Changes in Human Left and Right Atrial Conduction", Journal of Cardiovascular Electrophysiology, vol. 17, No. 2, pp. 120-127, (2006).
Shariat, M.H., "Cardiac Conduction Velocity Estimation from Sequential Mapping Assuming Known Gaussian Distribution for Action Time Estimation Error", IEEE, pp. 505-508, (2016).
Shariat, M.H., "Maximum Likelihood Cardiac Conduction Velocity Estimation from Sequential Mapping in the Presence of Activation Time Noice with Unknown Variances", IEEE, pp. 2745-2748, (2016).
Mongillo, M., "Choosing Basis Functions and Shape Parameters for Radial Basis Function Methods", SIAM Undergraduate Research Online, pp. 190-209, (2011).
Broomhead, D S., et al., "Multivariable Functional interpolation and Adaptive Networks", Royal Signals and Radar Establishment, Complex Systems Publications, Inc., pp. 321-355,(1988).
Broomhead, D.S. et al., "Radial Basis Functions, Multi-Variable Functional Interpolation and Adaptive Networks", Royal Signals & Radar Establishment, memorandum 4148, pp. 1-39, (1988).
Korenberg, M.J., et al., "Applications of Fast Orthoganol Search: Time-Series Analysis and Resolution of Signals in Noise", Annals. of Biomedical Engineering, vol. 17., pp. 219-231, (1989).
Tibshirani, R., "Regression Shrinkage and Selection via the Lasso", J.R . Statist. Soc. B, vol. 58, No. 1, pp. 267-288, (1996).
Chen, S. et al., "Orthogonal least-squares algorithm for training multioutput radial basis function networks", IEE Proceeding-F, vol. 139, No. 6, pp. 378-384, (1992).
El-Shafie, A., et al., "Fast orthogonal search (FOS) versus fast Fourier transmorm (FFT) as spectral model estimations techniques applied for structural health monitoring (SHM)", Struct Multidisc Optim, vol. 45, pp. 503-513, (2012).
Shariat, M.H. et al., "Bipolar Intracardiac Electrogram Active Interval Extraction During Atrial Fibrillation", IEEE Transactions on Biomedical Engineering, vol. 64, No. 9, pp. 2122-2133, (2017).
Shariat, M.H., "Processing the Intarcardiac Electrogram for Atrial Fibrillation Ablation", Thesis submitted to Queen's University, pp. 1-240. (2016).
Kuklik, P., et al., "Stability of Conduction Patterns in Persistent Atrial Fibrillation", Computing in Cardiology, vol. 44, pp. 1-4, (2017).
Shariat, M. H., "Activation Detection of Intracardiac Electrogram During Atrial Fibrillation Based on the Variance Equality Test", Proceeding of the IEEE 28th Canadian Conference on Electrical and Computer Engineering, pp. 387-391, (2015).

* cited by examiner

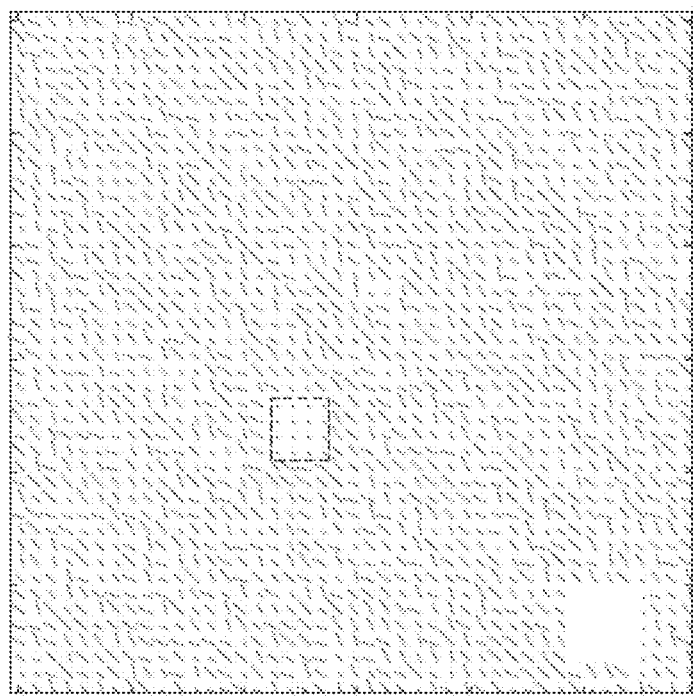
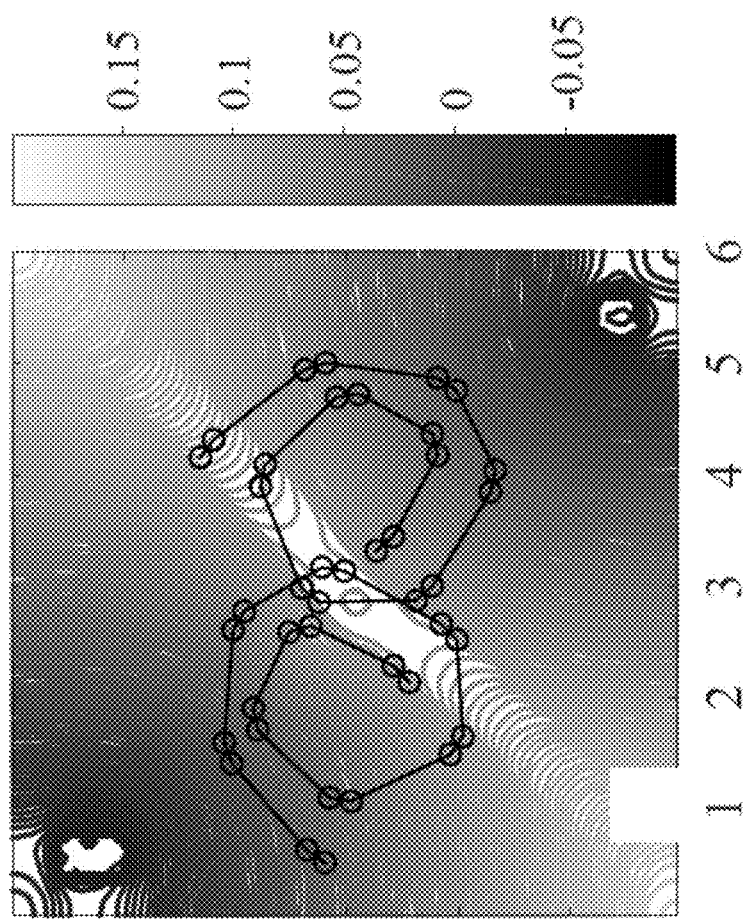
Fig. 1A
Fig. 1B

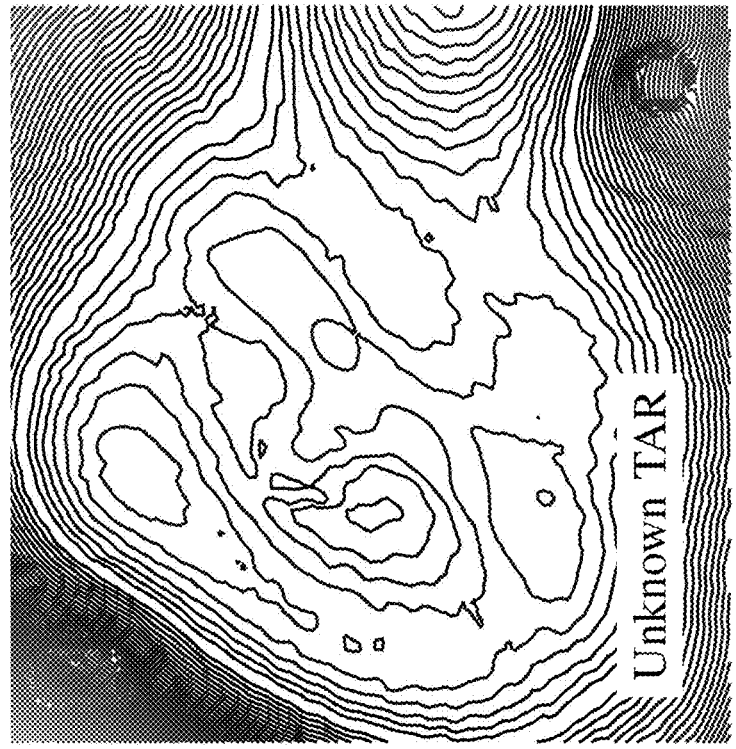
Fig. 4B
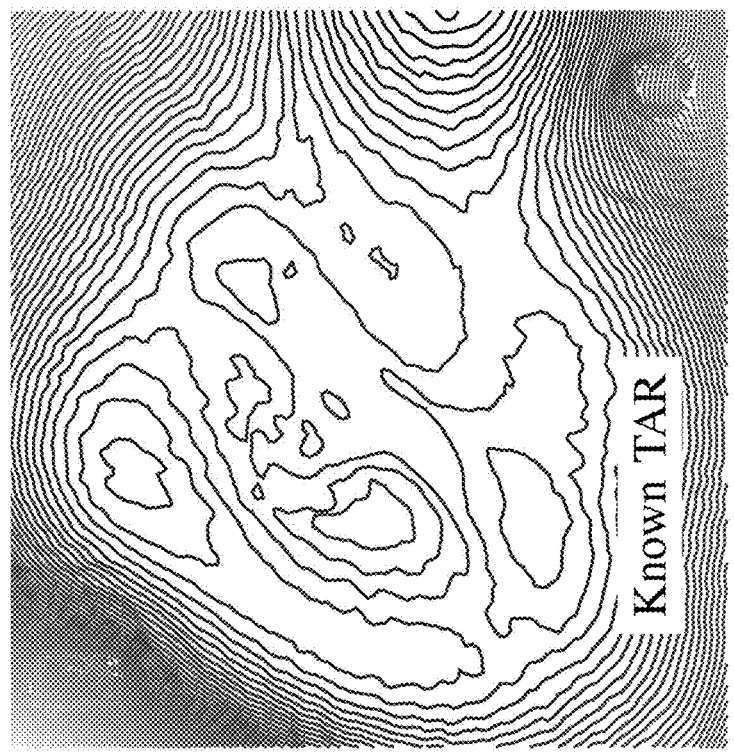
Fig. 4A
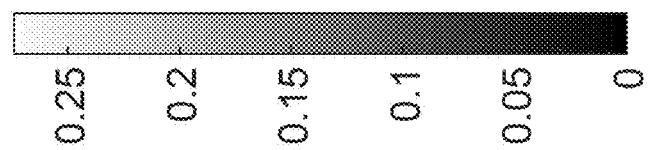

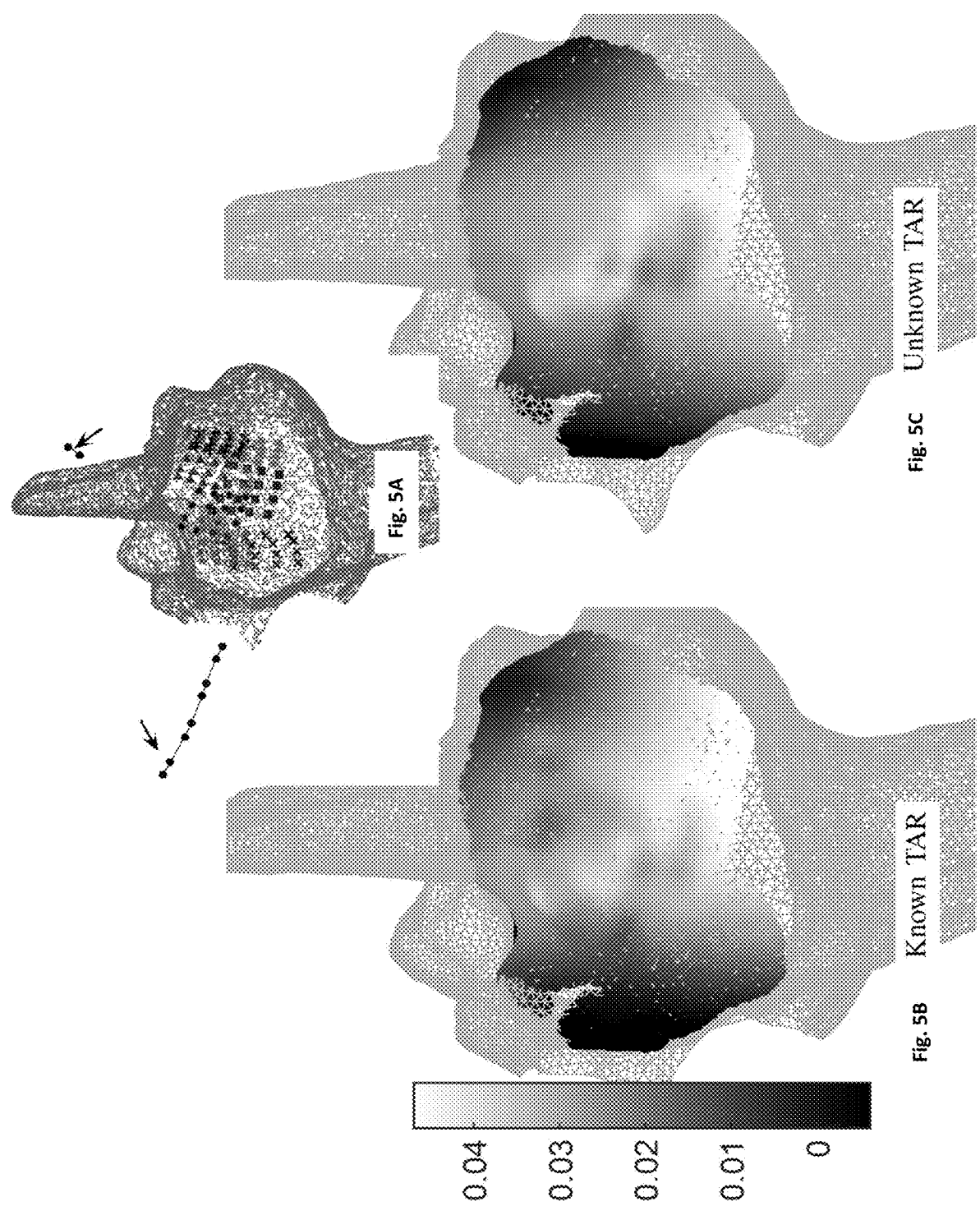

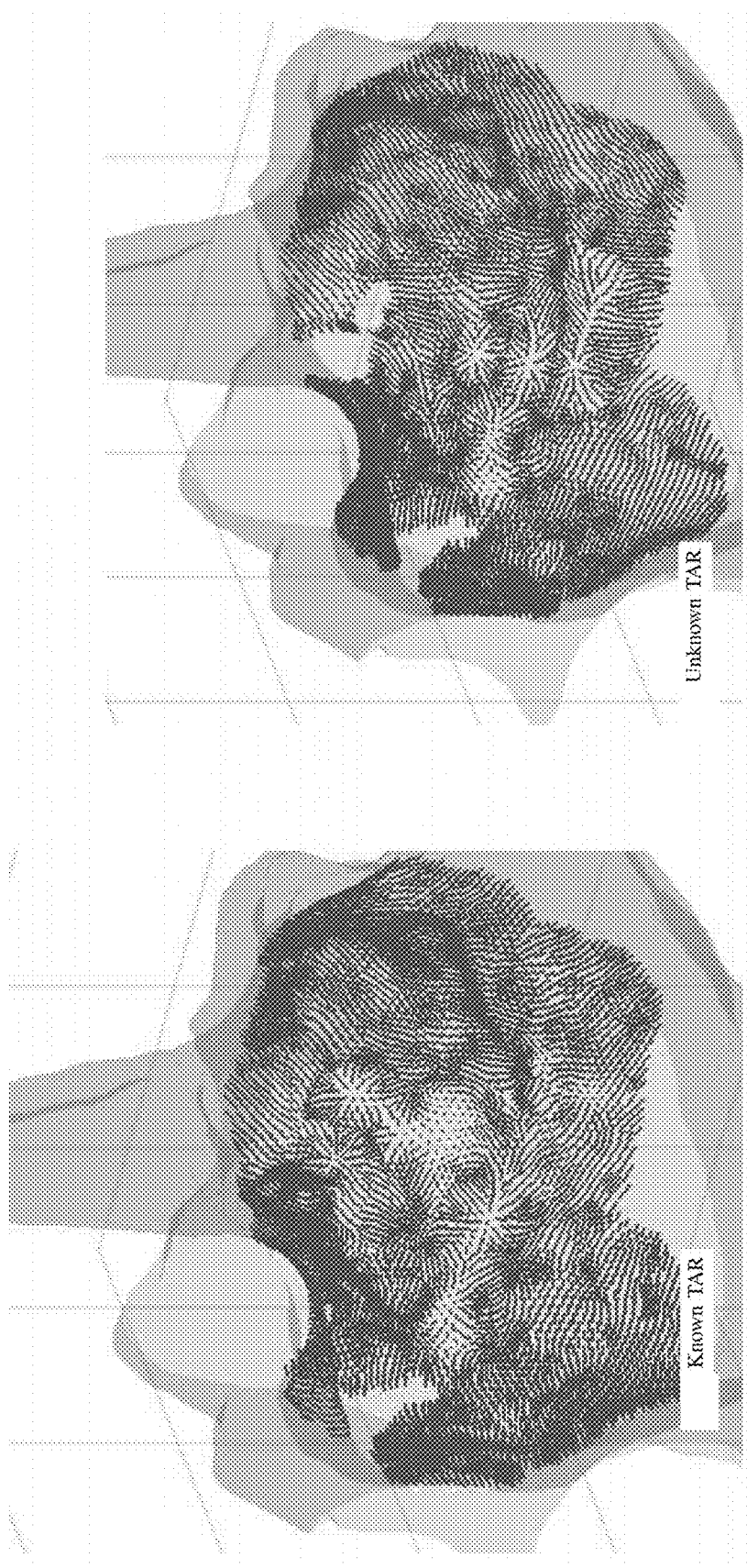

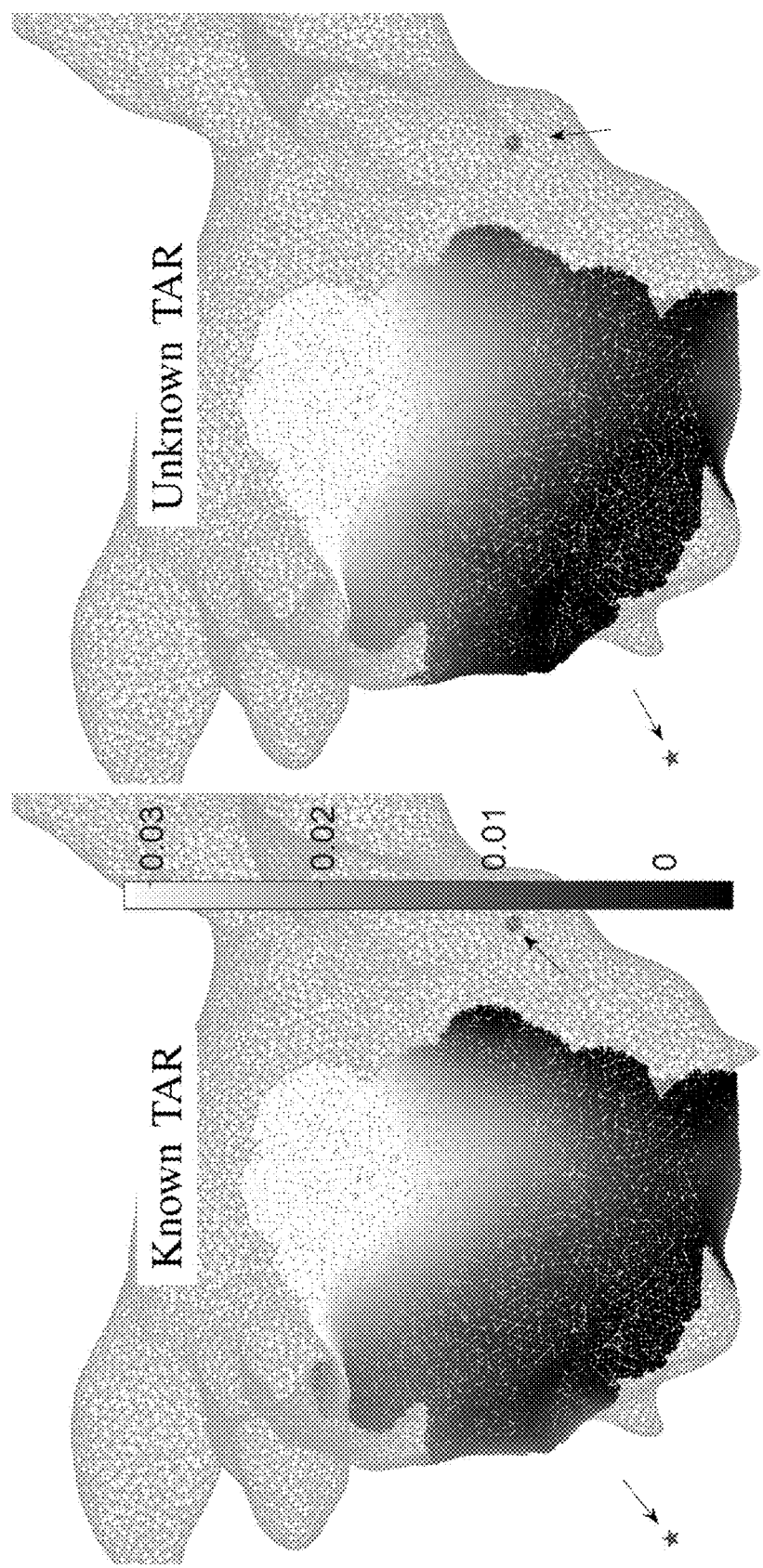

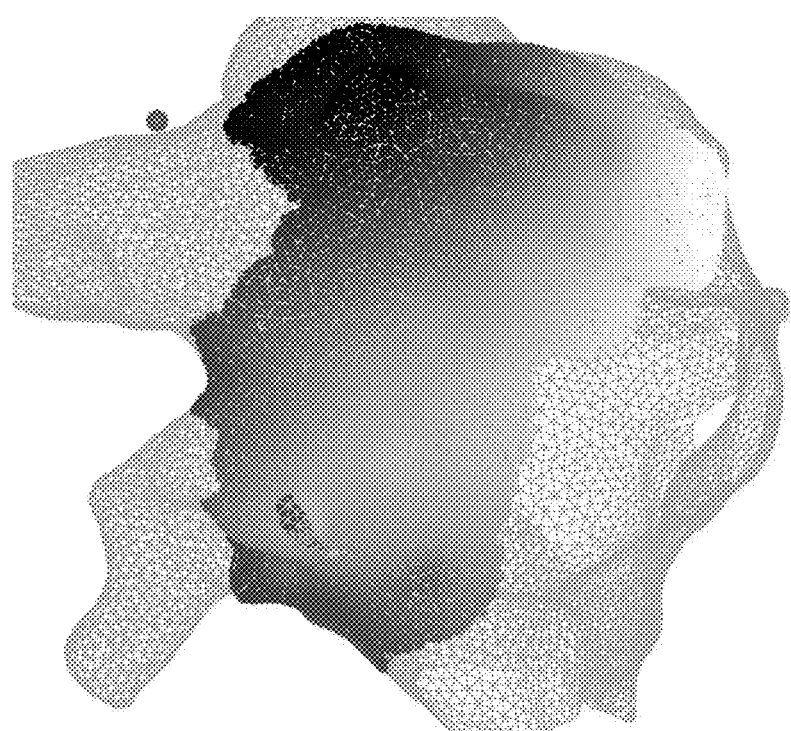
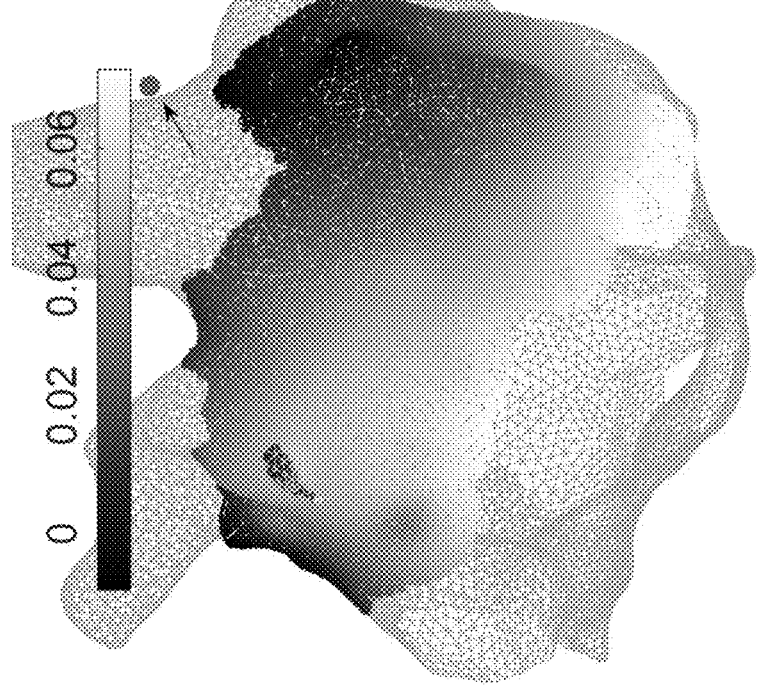
Fig. 9A  Known TAR
Fig. 9B  Unknown TAR

SEQUENTIAL MAPPING OF CARDIAC ARRHYTHMIA WITHOUT FIDUCIAL TIME REFERENCE

RELATED APPLICATION

This application claims the benefit of the filing date of Application No. 62/907,072, filed on 27 Sep. 2019, the contents of which are incorporated herein by reference in their entirety.

FIELD

This invention relates to methods for generating a propagation map for cardiac arrhythmia. More specifically, methods are provided for generating activation isochrones and propagation maps without the need for a time alignment reference. The methods simplify procedures for diagnosing cardiac arrhythmia, localizing cardiac arrhythmia, and guiding catheter ablation therapy of cardiac arrhythmia.

BACKGROUND

Various methods have been proposed to use intracardiac electrograms (EGMs) and the locations of electrodes of a catheter to estimate a propagation map and cardiac conduction velocity vectors at the desired sites [1-10]. Depending on the type of the available signals and the way the signals were recorded, such mapping methods are categorized into two types: continuous and sequential.

During continuous mapping, a large multipolar mapping catheter is used to simultaneously collect EGMs from a large portion of the targeted cardiac chamber. While this method enables fast cardiac mapping after processing a few wavefronts, drawbacks include limited maneuverability, incomplete endocardial coverage, undersampling and sub-optimal spatial resolution, and potential risk of systemic thromboembolism. In addition, large catheters are expensive and they are not useful to guide pulmonary vein isolation.

The most commonly used technique by physicians is sequential mapping where a small roving catheter, often with a high density of electrodes, is sequentially placed at different spatial locations within a desired cardiac chamber and the collected EGMs are used to create an activation map which informs the path of a reentrant circuit or location of a focal source. Since EGMs are collected sequentially, a reference EGM is required as a fiducial time reference to align the 'temporal phase' of collected EGMs. A catheter with electrodes fixed in space (and therefore fixed recording phase), such as in the coronary sinus (CS) or right ventricular apex, is frequently used for time synchronization. This is due to the spatial stability these locations afford and the ability to employ the relatively discrete intracardiac EGM rather than the surface ECG. Following that, the timing of the roving catheter EGMs is compared with the fixed fiducial reference and a 'local' activation time can be associated to each location. Given the common reference, the local activation times (LATs) of the EGMs can be combined to deliver a representation of the arrhythmia either static isochrone image or animated propagation.

These approaches commonly rely on different assumptions regarding the propagating wavefront shapes, and they deal with ambiguities in the recording sites differently [1-9]. In presence of a time alignment reference (TAR), currently available software for sequential mapping is able to generate propagation and isochrone maps during regular rhythms with homogenous frequency distribution throughout the chamber, such as atrial/ventricle tachycardia of fixed cycle lengths. However, time alignment using a remote EGM is not possible during complex arrhythmias such as atrial fibrillation (AF). During AF, multiple asynchronous wavefronts excite different atrial tissue simultaneously and the wavefront passing the roving mapping catheter might be different from the one that hits the TAR catheter, causing currently available methods for velocity vector estimation during sequential mapping to fail. In addition, the frequency distribution is heterogenous and variable, further reducing the utility of currently available methods.

SUMMARY

According to one aspect of the invention there is provided a method for generating a propagation map and a conduction velocity map for cardiac wavefront propagation, comprising: obtaining a set of local activation times (LATs) of electrograms and location coordinates of electrodes of a catheter; generating an activation time function (ATF) using candidate functions (CFs) selected from a bank of CFs, wherein weighting parameters of the CFs and time alignment references (TARs) are estimated to match available LATs of the electrodes; determining an ATF as a combination of the selected CFs, and using the ATF to generate propagation and conduction velocity maps of the cardiac wavefront propagation; wherein the propagation and conduction velocity maps are used for one or more of diagnosing cardiac arrhythmia, localizing cardiac arrhythmia, guiding catheter ablation therapy of cardiac arrhythmia, and guiding cardiac pacing therapy.

According to embodiments, the cardiac wavefront propagation may include cardiac arrhythmia, sinus rhythm, or paced rhythm.

One embodiment relates to a method for generating a propagation map and a conduction velocity map for cardiac arrhythmia, comprising: obtaining a set of local activation times (LATs) of electrograms and location coordinates of electrodes of a catheter; generating an activation time function (ATF) using candidate functions (CFs) selected from a bank of CFs, wherein weighting parameters of the CFs and time alignment references (TARs) are estimated to match available LATs of the electrodes; determining an ATF as a combination of the selected CFs, and using the ATF to generate propagation and conduction velocity maps of the cardiac arrhythmia; wherein the propagation and conduction velocity maps are used for one or more of diagnosing cardiac arrhythmia, localizing cardiac arrhythmia, and guiding catheter ablation therapy of cardiac arrhythmia.

In one embodiment, the generating the activation time function and the propagation map does not require using a reference catheter for time alignment.

In one embodiment, the ATF is a weighted summation of nonlinear, nonorthogonal, candidate functions (CFs) of coordinates of the electrodes of the catheter.

In various embodiments, the method comprises using a technique selected from exhaustive search, FOS, LASSO, and OLS to expand the activation time function as a linear combination of CFs.

In various embodiments, the method comprises using a computationally efficient selection method (CESM) for selecting CFs; and modifying the ATF by selecting additional CFs.

In one embodiment, the method comprises creating a low resolution propagation map by using a small number of CFs in the ATF; extracting time alignment shifts using the low resolution map; and generating a final propagation map by including a larger number of CFs in the ATF.

In one embodiment, the method comprises using the activation times to estimate the conduction velocity.

In one embodiment, the method comprises using an absolute error of the LATs and an activation map at different electrode placements to create an error map; wherein the error map shows reliability of the generated propagation map and identifies sites with complex signals and/or sites with low density of collected electrogram signals.

In one embodiment, the set electrograms is obtained simultaneously from a single catheter placement.

In one embodiment, the set of electrograms is obtained from two or more catheter placements during sequential recording, with unknown time shifts between different recording placements.

In one embodiment, the method comprises including a predefined binary level set of CFs in the output of the selected CFs; obtaining a constant value time shift of the activation times of the recordings; and identifying sequential TARs; wherein phase differences between sequential recording at different sites are compensated, and the sequential recording is transformed to continuous recording. The method may comprise using the selected CFs with a technique selected from FOS, LASSO, OLS, and CESM to identify the sequential TARs.

In one embodiment, the cardiac arrhythmia comprises atrial and ventricle flutter.

In one embodiment, the cardiac arrhythmia comprises atrial fibrillation.

In various embodiments, a processor is used to perform one or more function according to the methods described herein.

According to another aspect of the invention there is provided programmed media for use with a processor, comprising: code stored on non-transitory storage media compatible with the processor, the code containing instructions to direct the processor to: receive data corresponding to EGMs of electrodes of a catheter disposed in a sampled region of a subject; obtain a set of local activation times (LATs) of the EGMs and location coordinates of the electrodes of the catheter; generate an activation time function (ATF) using candidate functions (CFs) selected from a bank of CFs, wherein weighting parameters of the CFs and time alignment references (TARs) are estimated to match available LATs of the electrodes; determine an ATF as a combination of the selected CFs, and use the ATF to output propagation and conduction velocity maps of a cardiac wavefront propagation; wherein the propagation and conduction velocity maps are used for one or more of diagnosing cardiac arrhythmia, localizing cardiac arrhythmia, guiding catheter ablation therapy of cardiac arrhythmia, and guiding cardiac pacing therapy. According to embodiments, the cardiac wavefront propagation may include cardiac arrhythmia, sinus rhythm, or paced rhythm.

BRIEF DESCRIPTION OF THE DRAWINGS

For a greater understanding of the invention, and to show more clearly how it may be carried into effect, embodiments will be described, by way of example, with reference to the accompanying drawings, wherein:

FIG. 1A is a plot showing isochronal lines of a simulated wavefront propagation of two focal stimuli in an anisotropic region.

FIG. 1B is a plot showing diffusion coefficients at different grid points, represented with lines where the projections of each line on the x and y axes show the diffusion factor in that direction; a block of slow conduction region is marked with a dashed rectangle.

FIGS. 4A and 4B are plots showing absolute error of the isochronal map estimated using all the LATs during two catheter placements for a known TAR and unknown TAR, respectively, wherein FOS was used to properly combine C=7 Gaussian radial basis candidate functions.

FIGS. 5A-5C show results of sequential mapping using an Advisor™ HD Grid catheter when pacing was done simultaneously from CS and ablation catheters, wherein FIG. 5A shows the left atrium shell and the recording electrode locations indicated with different markers; FIGS. 5B and 5C show isochronal propagation maps when the TAR was used and when it was not available, respectively, according to a first example.

FIGS. 6A and 6B show estimated velocity vector direction maps in the presence and the absence of the TAR, respectively, for the example of FIGS. 5A-5C.

FIGS. 8A and 8B show isochronal propagation maps when pacing impulses were generated simultaneously from the CS and ablation catheters (marked with arrows), when the pacing signal was also used as a TAR and when the TAR was not available, respectively, for the example of FIGS. 7A-7B.

FIGS. 9A and 9B show isochronal propagation maps for a patient with atrial fibrillation when pacing impulses with were generated simultaneously using both CS and ablation catheters (marked with arrows), when the pacing signal was also used as a TAR and when the TAR was not available, respectively.

DETAILED DESCRIPTION OF EMBODIMENTS

Figure 2A:
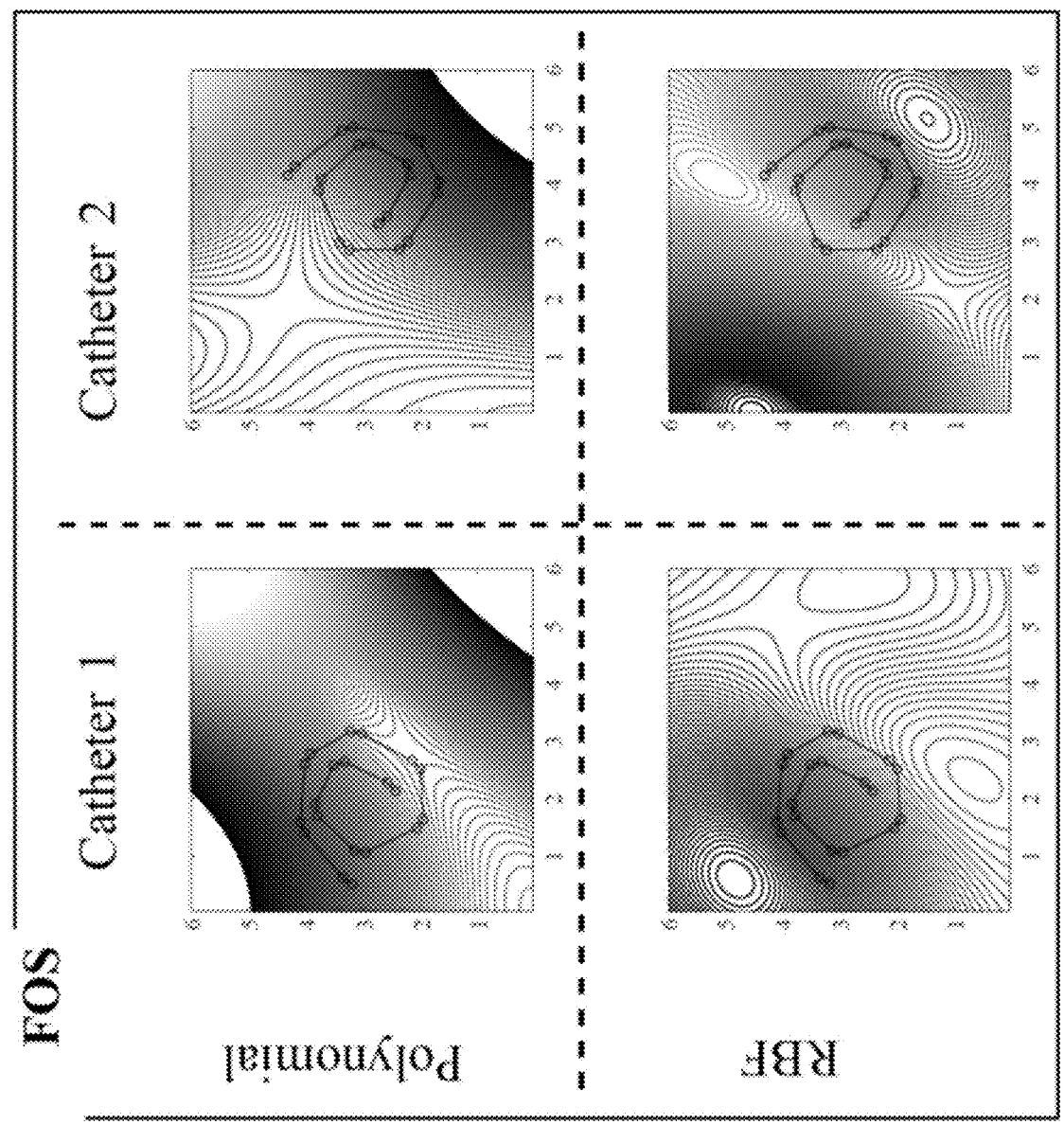
FIGS. 2A and 2B show estimated isochronal lines of a simulation when only LATs of a single catheter placement were used, for scenarios where a bank of CFs either contains 3rd-order polynomial functions or Gaussian RBFs centered around the locations of the recording points, wherein results are plotted for FOS (FIG. 2A) or LASSO (FIG. 2B) used to combine C=4 terms to expand the ATF.

Information regarding activation of complex arrhythmia is crucial to successful treatment using standard catheter ablation techniques. Prior techniques require substantial data collection, which is time consuming, and they rely on additional information from electrodes of a catheter in a stable location to provide a time alignment reference. However, displacement of the stable catheter can result in erroneous results, and moreover, a change in rhythm requires significant time commitment to set up the condition necessary to create a propagation map.

Embodiments described herein overcome drawbacks of prior techniques by substantially automating the mapping process and avoiding the need for an additional, stable reference catheter. Embodiments are adaptable to change in rhythm without lengthy and time-consuming set up tasks. For example, a focal discharge from the right ventricular outflow tract may be mapped and location accurately determined with a single catheter immediately upon introduction of the catheter to the chamber. Regular atrial tachycardias, flutters, and focal sources can be located and determined with little human intervention and without the need for an additional reference catheter. Further, embodiments provide the ability to map irregular, complex arrhythmias, e.g., tachycardias, such as atrial fibrillation, and may also be used to map sinus rhythm and paced rhythm. The propagation and conduction velocity maps may be used in diagnostic and therapeutic applications, including, but not limited to, diagnosing cardiac arrhythmia, localizing cardiac arrhythmia, guiding catheter ablation therapy of cardiac arrhythmia, and guiding cardiac pacing therapy. Accordingly, embodiments provide a significant advance over prior techniques, and provide both time and cost savings.

Described herein is a method for generating an activation isochrone and propagation map of cardiac wavefront propagation in the absence of any fiducial TAR. Embodiments include activation time function estimation using the LATs and locations of electrodes of the catheter when only EGMs from a single catheter placement site are available. Further embodiments are able to generate a propagation map using multiple sequential recordings. Embodiments do not use an independent EGM (e.g., from a CS catheter or a surface ECG) as a TAR. Instead, only local sequential recordings are used to identify the isochronal map.

1.0 Method (Single Catheter Placement)

The activation time function (ATF) assigns an activation time to any input coordinate. Here, it is assumed that the ATF is a weighted summation of several nonlinear, nonorthogonal, candidate functions (CFs) of coordinates of the electrodes of the catheter. In this section, the recording signals from a single catheter placement were used to obtain an isochronal map. The problem formulation for the propagation map extraction using the LATs of the electrodes of the catheter when it is placed at only one site is presented in Section 1.1. Sample CFs are provided in Section 1.2. Section 1.3 shows embodiments for efficient methods to select CFs and properly combine them to estimate the ATF.

1.1 Problem Formulation

The goal in this section is to estimate the activation time at $p=[x, y, z]^T$ using only the LATs of the electrodes obtained during the sth catheter placement. It is assumed that the estimated activation time at the coordinate p, denoted by $\hat{T}(p^T)$, is the summation of C potentially nonlinear and nonorthogonal functions of p as described below:

$$\hat{T}(p^T)=\Sigma_{i=1}^{C}\alpha_i\Phi_i(p^T), \quad (1)$$

where $\Phi_i(\bullet)$ for i=1, . . . , C are CFs used to expand the activation time and $\{\alpha_{i=1}\}^{N_s}$ ($\alpha_i$ for i=1, . . . $N_s$) are weighting/combining coefficients. It is assumed that C, the total number of CFs, is known and CFs can be selected from a given bank of CFs. In Section 1.2 sample functions to create a bank of CFs are presented. In order to obtain ATF $\hat{T}(\bullet)$, proper CFs and combining parameters should be determined such that $\hat{T}$ evaluated at the electrodes become close to their measured LATs. That is, if $p_{s,j}$, for j=1, . . . , $N_s$, shows the location of jth electrode in contact to the tissue at the sth sequential recording site, then $\hat{T}$ should be determined to minimize the following least squared (LS) error $$\Sigma_{j=1}^{N_s}(\text{LAT}(p_{s,j}^T)-\hat{T}(p_{s,j}^T))^2=\|\text{LAT}(P_s)-\hat{T}(P_s)\|^2, \quad (2)$$

where $\text{LAT}(p_{s,j}^T)$ is the LAT at $p_{s,j}$, and $P_s=[p_{s,1}, \ldots, p_{s,N_s}]^T \in \mathbb{R}^{N_s \times 3}$; LAT $(P_s)$ and $\hat{T}(P_s)$ are used to denote $N_s$-dimensional vectors that their kth row, respectively, shows the measured LAT and the ATF at the electrode located at the kth row of $P_s$ (i.e., the LAT at $p_{s,k}$).

1.2 Sample Candidate Functions

The considered model for the ATF (equation 1) describes very diverse patterns of wavefront propagation. The considered models for activation function in some previously proposed methods (e.g., [2-7]) can be interpreted as special cases of (1) wherein a predetermined sets of functions are used to expand the ATF. Such functions are included in the created bank of CFs presented herein; the ATF is expanded by properly combining selected functions from all the available CFs.

The expansion of ATF using a radial basis function (RBF) is considered in [11, 12]; this is a special case of (1) in which $C=N_s$, $\Phi_i(p^T)=\Phi_\in(\|p-p_{s,i}\|)$, for i=1, . . . $N_s$, where $\Phi_\in$ is an RBF with the shape parameter $\in$. Table 1 shows some common RBFs. In this approach $\Phi_i(p^T)$ are preset/fixed, and unknown weighting coefficients $\{\alpha_i\}_{i=1}^{N_s}$ are determined to minimize the LS error in (2).

Another special case of (1) is when the ATF is expanded using the RBF with augmented polynomial, i.e., in this case, for i=1, . . . , $N_s$, $\Phi_i(p^T)$ becomes an RBF which is only a function of $\|p-p_{s,i}\|$, and $\Phi_i(p^T)$ for i=$N_s$+1, . . . , $N_s$+M, are M polynomial terms. For example, for the cubic RBF with augmented polynomial [2], $\hat{T}(p^T)$ is expressed as $\Sigma_{i=1}^{N_s+4}\alpha_i\Phi_i(p^T)$ where $\Phi_i(p^T)=\|p-p_{s,i}\|^3$, for i=1, . . . , $N_s$, and $\Phi_i(p^T)$ for i=$N_s$+1, . . . , $N_s$+4, are x, y, z, and 1. Unknown $\{\alpha_i\}_{i=1}^{N_s+4}$ are specified by minimizing (2) while satisfying the following orthogonality condition:

$$\Sigma_{i=1}^{N_s}\alpha_i\Phi_j(p_{s,i}^T)=0, \text{ for } j=N_s+1, \ldots, N_s+4. \quad (3)$$

Expansion of the activation time when the wavefront propagation is assumed to be locally planar is considered in [5-7]. The formulation considered in these papers is also a special case of (1) where the activation time is a weighted combination of x, y, z and 1, i.e., $\hat{T}(p^T)=\alpha_1 x+\alpha_2 y+\alpha_3 z+\alpha_4$ and the unknown parameters $\alpha_i$ can be estimated by minimizing (2).

Another example of a special case of (1) is when the activation time is expanded using second-order polynomial functions [3, 4]; in this case, C=10 and $\Phi_j(p^T)$ for j=1, . . . , 10 are $x^2$, $y^2$, $z^2$, xy, xz, yz, x, y, z, and 1. Similarly, the unknown $\{\alpha_i\}_{i\pm 1}^{10}$ can be estimated from the LS fitting of $\text{LAT}(p_{s,i}^T)$ and $\hat{T}(p_{s,i}^T)$ and minimizing (2).

Previous examples confirm that different functions can be used for the expansion of the ATF. It is not clear which set of functions is a better choice for expanding the ATF; this makes the performances of the aforementioned methods case sensitive as they are highly influenced by the number and quality of the available LATs at the recording sites, as well as the underlying complexity of the arrhythmia. Therefore, in embodiments described herein, a bank of CFs is created which consists of different sets of CFs. The proper functions are then selected from the bank of CFs (as described in the next section) and their weighting parameters are designed to properly match the available LATs of electrodes. Sample functions include $x^{k_x} y^{k_y} z^{k_z}$ (e.g., x, y, z, xy, xz, yz, $x^2$, $y^2$, $z^2$) and $\Phi_\in(r_i)$ where $r_i = \|p - p_i\|$ for $i=1, \ldots, N_s$ when $p_i$ is the location of the ith known LAT site and $\Phi_\in$ can be different RBFs such as those presented in Table 1.

TABLE 1

Examples of common radial basis functions (RBFs)[11, 13]

| RBF | $\Phi_\epsilon(r)$ |
|---|---|
| Gaussian (GA) | $e^{-(\epsilon r)^2}$ |
| Multiquadratic (MQ) | $\sqrt{1+(\epsilon r)^2}$ |
| Inverse Multiquadratic (IM) | $(1+(\epsilon r)^2)^{-1/2}$ |
| Inverse Quadratic (IQ) | $(1+(\epsilon r)^2)^{-1}$ |
| Linear | $\epsilon r$ |
| Cubic | $\epsilon r^3$ |
| Thin plate spline | $r^2 \ln(\epsilon r), 0 < \epsilon \leq 1$ |
| $C^0$ Matérn | $e^{-\epsilon r}$ |
| $C^2$ Matérn | $e^{-\epsilon r}(1+\epsilon r)$ |
| $C^4$ Matérn | $e^{-\epsilon r}(3+3\epsilon r+(\epsilon r)^2)$ |

1.3 Candidate Functions Selection

In (1), it was assumed that the ATF can be expressed as a combination of multiple CFs which are selected from a bank of CFs. If C and the total number of CFs in the bank are small values, the exhaustive search among all the possible combinations of CFs can be evaluated to find the best set of CFs. However, this method cannot be used when there is limited computation power or a large number of CFs to choose from. This problem becomes more challenging when C, the total number of CFs that are used to expand the ATF, is unknown. Other methods such as fast orthogonal search (FOS) [14], least absolute shrinkage and selection operator (LASSO) [15], or orthogonal least square (OLS) [16] can be used to expand the ATF as a linear combination of a proper set of CFs. The FOS method is a computationally efficient method to find expansion of a function as combination of non-orthogonal CFs and is mainly used in the next section. In every step of FOS, the CF that results in the maximum reduction of the LS fitting error is identified and properly combined with the previously selected CFs [14, 17].

To summarize, according to a generalized embodiment, a bank of CFs is generated and an appropriate set of CFs is selected and combined to accurately match the known LATs at the recording sites. An example of a pseudo-code that describes the generalized approach is as shown below:

Input: Locations and LATs of electrodes at the sth catheter placement, i.e., $P_s$ & LAT ($P_s$).

Output: Conduction velocity, v, and ATF, $\hat{T}$, at $p=[x, y, z]^T$.

Bank of Candidate Functions (CFs): Generate different CFs (e.g., see Section 2.2).

Activation Time Function: Use a method (e.g., exhaustive search, FOS, LASSO, or OLS) to expand $\hat{T}(p^T)$ as a linear combination of CFs, to minimize the least squared error between LAT($P_s$) and $\hat{T}(P_s)$.

Conduction Velocity: Use $\hat{T}(p^T)$ to estimate v [4]:

$$\tilde{v} = \left[\frac{\partial \hat{T}(p^T)}{\partial x}, \frac{\partial \hat{T}(p^T)}{\partial y}, \frac{\partial \hat{T}(p^T)}{\partial z}\right]^T, v(p) = \frac{\tilde{v}}{\|\tilde{v}\|^2}. \quad (4)$$

2 Sequential Recording

In sequential mapping, a roving catheter collects EGMs from different sites one after another and the LATs of EGMs are extracted and are used for the CV estimation. A stable EGM from a fixed catheter is usually deployed as a fiducial reference for time synchronization of recordings at different sites during sequential recordings. However, embodiments described herein do not require the use of a fiducial reference EGM that is placed far from the recording site. Instead, it is assumed that the adjacent recordings using the mapping catheter are results of stable wavefront propagations, i.e., it is assumed that the sequential recordings were done during different 'phases' of stable wavefront propagation. The goal is to combine all the sequential recordings to estimate the ATF and consequently, to generate isochronal and velocity maps. Unlike the previous section where all the EGMs were collected simultaneously, during sequential recording there exist unknown time shifts (also known as recording phases) between different recording sites. Embodiments described in this section are able to identify the time shifts between recordings and at the same time obtain the ATF, D.

Consider a cardiac mapping in which EGMs from S sites were sequentially collected, where at sth site $N_s$ electrodes of the catheter were in contact with the tissue. Consequently, a total of $N = \Sigma_{i=1}^{S} N_i$ local activation times are collected from electrodes at different sites and this information is used to estimate the ATF.

For $s=1, \ldots, S$, define $P_s = [p_{s,1}, \ldots, p_{s,N_s}]^T \in \mathbb{R}^{N_s \times 3}$ where rows of $P_s$ are the coordinate locations of $N_s$ electrodes in contact with the tissue at the sth sequential catheter placement. LAT($P_s$) and $\hat{T}(P_s)$ are used to denote $N_s$-dimensional vectors that their kth row, respectively, shows the measured LAT and the ATF at $p_{s,k}$ (the kth row of $P_s$).

The following equation describes the relationship between the measured LAT and the ATF:

$$LAT(P_s) = \hat{T}(P_s) + t_{1,s} 1_{N_s}, \text{ for } s=1, \ldots, S \quad (5)$$

where $t_{1,s}$ for $s=1, \ldots, S$ is the unknown time alignment shift between the first and sth recording site and $t_{1,1}=0$. The following objective function can be minimized to express $\hat{T}(p^T)$ as a linear combination of the CFs such that it properly matches the measured LATs during sequential recordings, $$\min_{\{t_{1,s}\}_{s=2}^{S}, \hat{T}(\cdot)} \sum_{s=1}^{S} \|LAT(P_s) - \hat{T}(P_s) - t_{1,s} 1_{N_s}\|^2. \quad (6)$$

Define $P \in \mathbb{R}^{N \times 3}$ as $P = [P_1^T, \ldots, P_S^T]^T$ which consists of all the electrodes' locations during the entire sequential recording. Use P to express (6) as $$\min_{\{t_{1,s}\}_{s=2}^{S}, \hat{T}(\cdot)} \|LAT(P) - \hat{T}(P) - \sum_{s=2}^{S} t_{1,s} q_s\|^2 \quad (7)$$

where $$q_s = [0_{\Sigma_{k=1}^{s-1} N_k}^T, 1_{N_s}^T, 0_{\Sigma_{k=s+1}^{S} N_k}^T]^T \in \mathbb{R}^{N \times 1},$$

in which $0_J$ and $1_J$ are the J-dimensional vectors of zeros and ones, respectively. Similar to the previous section, it is assumed that the ATF is a linear combination of the CFs. Thus, (7) can be expressed as $$\min_{\{\alpha_i,\Phi_i\}_{i=1}^{C},\{t_{1,s}\}_{s=2}^{S}} \left\| LAT(P) - \sum_{i=1}^{C} \alpha_i \Phi_i(P) - \sum_{s=2}^{S} t_{1,s} q_s \right\|^2. \quad (8)$$

In (8), $\Phi_i(P)$ is an N-dimensional vector, where its kth element is obtained by applying $\Phi_i$ to the kth row of P. The above equation can be written as $$\min_{\{\alpha_i\}_{i=1}^{C+S-1},\{\Phi_i\}_{i=1}^{C}} \left\| LAT(P) - \sum_{i=1}^{C+S-1} \alpha_i \Phi_i(P) \right\|^2. \quad (9)$$

where $\alpha_i$ for $i=1, \ldots, C+S-1$ are unknown constants, $\Phi_j$ for $j=1, \ldots, C$, are CFs selected from a bank of CFs; whereas, for $j=C+1, \ldots, C+S-1$, $\Phi_j(P)=q_{j-C+1}$, which are not functions of P. Equation 9 shows that for the ATF estimation during sequential mapping, $q_2, \ldots, q_S$ should be included among the output of the selected CFs and then follow the same procedure as described in the previous section. Note that according to (9) adding $\kappa q_s$ to the ATF is equivalent to removing a constant value K from all the LATs extracted from the sth recording site, i.e., a constant value time shift of the activation times of sth recording can be obtained by embedding $q_s$ among selected CFs. Indeed, by including qs in the output of the selected CFs, the FOS, LASSO, or OLS method automatically identifies sequential TARs and compensates the phase differences between sequential recording at different sites, and this transforms the sequential recording to continuous recording (simultaneous recording from all available points). In the results section below the FOS method is used for the CF selection during sequential mapping, and includes all the necessary $q_i$ among the initial selected CFs.

3 Results

Using synthetic and clinical EGMs collected during a diagnostic electrophysiological study, the feasibility of the embodiments in the presence of multiple wavefronts (pacing from multiple sites) and absence of any TAR is confirmed.

In the first part of this section (4.1) a simple computer model was used to synthesize EGMs and to study the method during the collision of two wavefronts. Following that in Section 4.2, several clinical examples of propagation and velocity vector maps generated during pacing from two sites are provided. Embodiments are compared with the gold standard approach which uses a TAR EGM from the CS catheter.

4 Computer Model

To simulate the electrical activities of cardiac cells monodomain modified FitzHugh-Nagumo equations were used in two-dimensions (2D), with membrane parameters described in Table I of [18]. The corresponding 2D reaction-diffusion partial differential equations with Neumann no-flux boundary conditions were numerically solved (on 128× 128 grid points) by the finite difference method, and the diffusion terms were calculated using a five-point formula. Ghost points were deployed to include the Neumann boundary conditions [19], and the Euler method of integration were implemented to solve the differential equations [20]. Unipolar EGMs were calculated with sampling frequency of 1000 Hz using current source approximation for a large volume conductor [21]. For each electrode, the maximum negative slope of the unipolar signal (considered the most accurate marker of local tissue activation [1]) was identified as the electrode LAT, and consequently the LATs of all electrodes of the catheter were deployed to extract isochronal lines. The diffusion coefficients were selected to be constant in time, but not in space; that is, anisotropy was incorporated in the model by using a different diffusion constant at each point. Diffusion coefficients for the simulated model are represented with small lines in FIG. 1B, where the projections of each line on x and y axis shows the diffusion in that direction. A block of a slow conduction region is also included in the model as shown in FIG. 1B. For this simulation two focal stimuli that start their activations from opposite corners of the simulated region, simultaneously, were considered. The generated wavefronts of two sources then collide along the diagonal as shown in FIG. 1A.

Figure 2B:
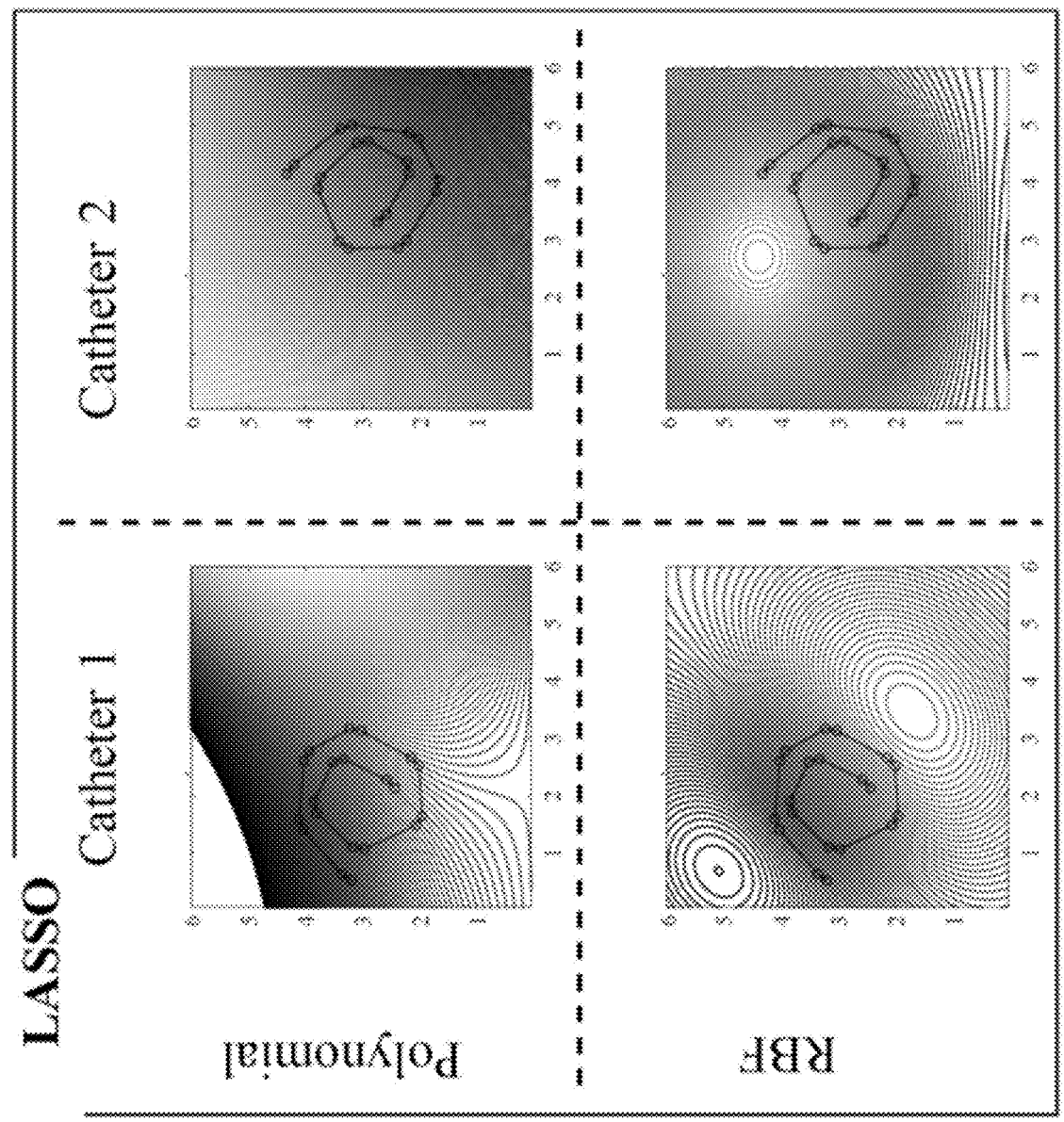

FIGS. 2A and 2B show the estimated isochronal lines of the described simulation when only LATs of a single catheter placement were used. The results are reported for scenarios where the bank of CFs either contains $3^{rd}$ order polynomial functions or Gaussian RBFs centered around the locations of the recording points. The results are plotted for FOS (FIG. 2A) or LASSO (FIG. 2B) used to combine C=4 terms to expand the ATF.

Figures 3A, 3B:
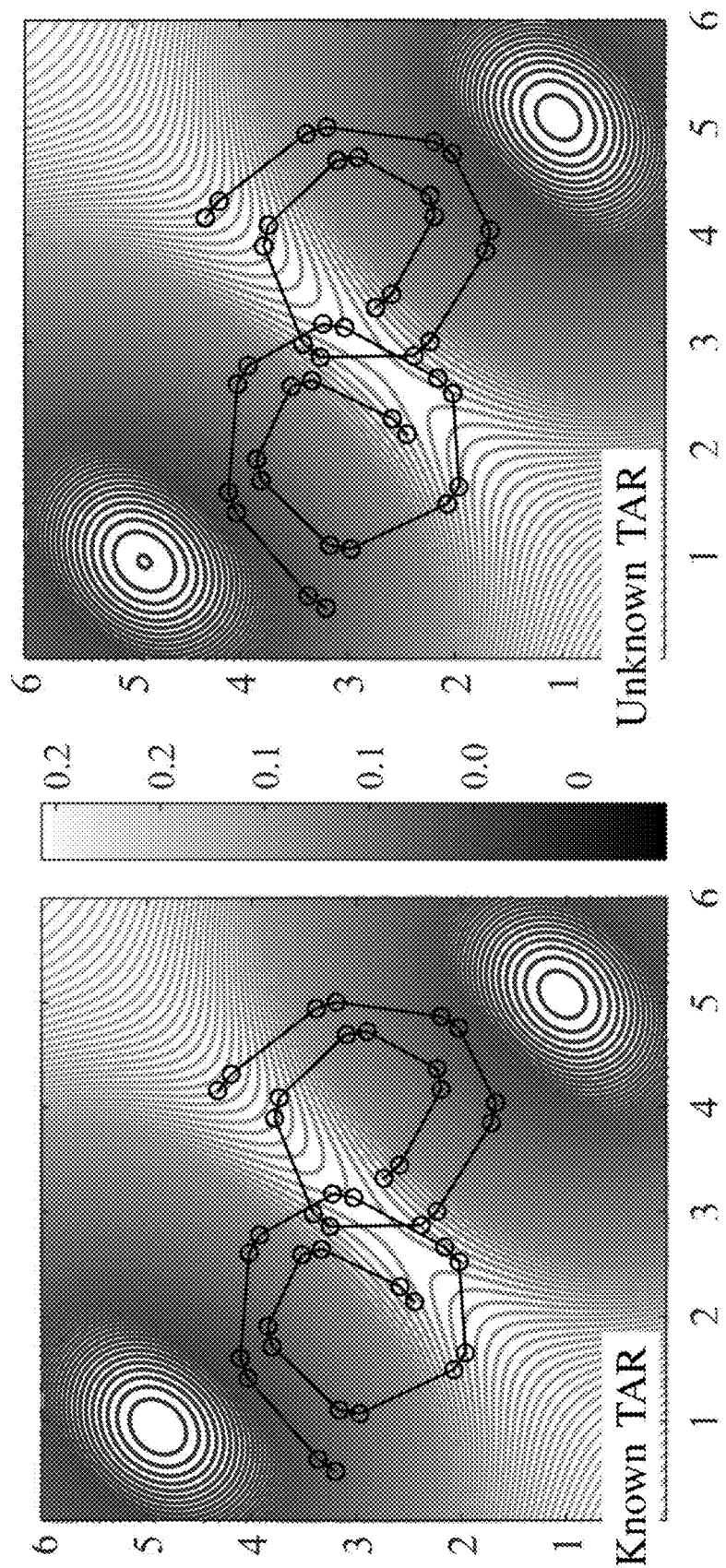
FIGS. 3A and 3B are isochronal maps estimated using all the LATs during two catheter placements for a known TAR and unknown TAR, respectively, wherein FOS was used to properly combine C=7 Gaussian radial basis candidate functions.

FIG. 3 shows the isochronal maps estimated using all the LATs during both catheter placements. Here, the bank of CFs only included Gaussian RBFs centered around the recording points and C=7.

FIG. 4 shows the absolute error of the estimated isochronal map using the LATs of the catheter at both recording sites in the simulated region. The FOS were used to properly combine C=7 Gaussian radial basis candidate functions.

5.1 Finding the Number of Terms in the ATF Expansion

The total number of terms in the ATF expansion, C, is an important parameter that can significantly impact the accuracy of the ATF. In practice, C can be selected based on the size of the mapping region and/or the density of measured points (overlap between catheter placements). Increasing C decreases training error, i.e., it decreases the relative LS error and mismatch between the values generated by ATF and those measured at the electrode sites. However, if a large number is selected for C, it might result in over-fitting and consequently, deviation from the true activation times at other points (avoid generalization) [23]. Different methods such as various types of cross validation can be used to select this parameter [11, 16, 24].

5.2 Partial Surface Mapping

Note that the RBF reaches its maximum at its center point and decreases as its argument deviates from that point, e.g., the Gaussian RBF exponentially decreases as its argument deviates from its center point. Therefore, when the RBFs are used for the ATF expansion, we can expect that the activation time of each point mainly is determined by its adjacent and close by known LATs. Consequently, the available points with known LATs may be divided into clusters and an embodiment can be applied to each part to create a propagation map. The selected CFs for each cluster are then included in the final mapping and the weighting factors can be recalculated after adding a few extra CFs from previously non-chosen CFs. Because of the small size of each cluster, embodiments employing this approach have significantly reduced complexity.

5.3 Reliability of the Produced Map

Following estimation of an ATF, performance can be evaluated by analysing the error between the measured LATs and predicted times. The absolute difference between the measured active times and those obtained using an estimated ATF can be shown on a map; the map shows sites that ATF properly describes the wavefront propagation, and also can be used to identify sites where ATF is unable to predict the activation times. This reliability map can be used to study the complexity of wavefront propagation, or to guide further data collection.

6 Implementation

Embodiments may be implemented at least partially in software (e.g., an algorithm). The software may include programmed media for use with a processor (e.g., a computer) and with data such as, for example, EGM data from electrodes, the programmed media comprising a computer program stored on non-transitory storage media compatible with the computer, the computer program containing instructions to direct the processor 1401 (FIG. 14) to perform one or more of the functions described above and/or in the embodiment of FIG. 14.

The computer may include a data processing system that controls one or more components of the system, in conjunction with a user interface (e.g., a graphical user interface (GUI)). Controlling may include functions such as receiving input (e.g., EGM data), analyzing data, and displaying results and/or images on a display of the system. The data processing system may be a client and/or server in a client/server system. For example, the data processing system may be a server system or a personal computer (PC) or tablet-based system. The data processing system may include an input device, a central processing unit (CPU), memory, display device, and interface device. The input device may include a keyboard, a mouse, a trackball, a touch sensitive surface or screen, or a similar device. The display may include a computer screen, television screen, display screen, terminal device, a touch sensitive display surface or screen, or a hardcopy producing output device such as a printer or plotter. The memory may include a variety of storage devices including internal memory and external mass storage typically arranged in a hierarchy of storage as understood by those skilled in the art. For example, the memory may include databases, random access memory (RAM), read-only memory (ROM), flash memory, and/or disk devices. The interface device may include one or more network connections. The data processing system may be adapted for communicating with other data processing systems over a network via the interface device. For example, the interface device may include an interface to a network such as the Internet and/or another wired or wireless network (e.g., a wireless local area network (WLAN), a cellular telephone network, etc.). Thus, the data processing system may be linked to other data processing systems by the network. The CPU may include or be operatively coupled to dedicated coprocessors, memory devices, or other hardware modules. The CPU is operatively coupled to the memory which stores an operating system for general management of the system. The CPU is operatively coupled to the input device for receiving user commands or queries and for displaying the results of these commands or queries to the user on the display. Commands and queries may also be received via the interface device and results may be transmitted via the interface device. The data processing system may include a database system (or storage) for storing data and programming information. The database system may include a database management system and a database and may be stored in the memory of the data processing system. In general, the data processing system has stored therein data representing sequences of instructions which when executed cause certain steps of the method described herein to be performed. For example, the instructions may be associated with one or more components of FIG. 1. Of course, the data processing system may contain additional software and hardware, a description of which is not necessary for understanding the invention.

Figure 14:
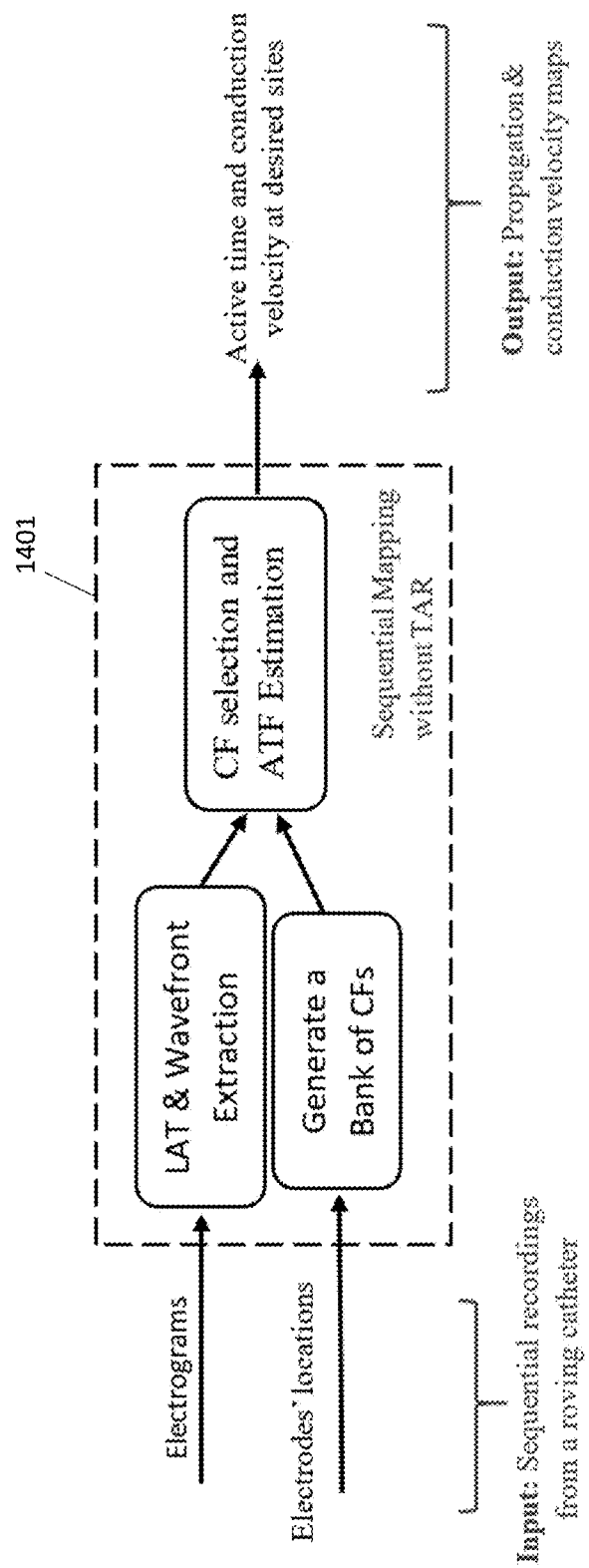
FIG. 14 is a flow chart showing a process according to an embodiment described herein.

Thus, the data processing system includes computer executable programmed instructions for directing the system to at least partially implement embodiments of the invention. Executing instructions may include the system prompting the user for input at various steps, some of which are shown in the embodiment of FIG. 14. In one embodiment, e.g., as shown in FIG. 14, the programmed instructions may be embodied in one or more hardware modules or software modules resident in the memory of the data processing system including a processor 1401 that executes the programmed instructions, or elsewhere. In one embodiment the programmed instructions may be embodied on a non-transitory computer readable storage medium or product (e.g., a compact disk (CD), etc.) which may be used for transporting the programmed instructions to the memory of the data processing system and/or for executing the programmed instructions. In one embodiment the programmed instructions may be embedded in a computer-readable signal or signal-bearing medium (or product) that is uploaded to a network by a vendor or supplier of the programmed instructions, and this signal or signal-bearing medium may be downloaded through an interface to the data processing system from the network by end users or potential buyers.

A user may interact with the data processing system and its hardware and software modules using a GUI. The GUI may be used for controlling, monitoring, managing, and accessing the data processing system. GUIs are supported by common operating systems and provide a display format which enables a user to choose commands, execute application programs, manage computer files, and perform other functions by selecting pictorial representations known as icons, or items from a menu through use of an input device such as a mouse or touch screen. In general, a GUI is used to convey information to and receive commands from users and generally includes a variety of GUI objects or controls, including icons, toolbars, drop-down menus, text, dialog boxes, buttons, and the like. A user typically interacts with a GUI presented on a display by using an input device (e.g., a mouse or touchscreen) to position a pointer or cursor over an object (e.g., an icon) and by "clicking" on the object. Typically, a GUI based system presents application, system status, and other information to the user in one or more "windows" appearing on the display. A window is a more or less rectangular area within the display in which a user may view an application or a document. Such a window may be open, closed, displayed full screen, reduced to an icon, increased or reduced in size, or moved to different areas of the display. Multiple windows may be displayed simultaneously, such as: windows included within other windows, windows overlapping other windows, or windows tiled within the display area.

Embodiments will be further described by way of the following non-limiting Examples.

7 Clinical Examples

Provided below are multiple examples of propagation maps for patients presented to the electrophysiology laboratory for a diagnostic electrophysiologic study and catheter ablation procedure. The left atrium of patients was mapped using an electroanatomic mapping system (EnSite™ Velocity™ system, St Jude Medical, MN). A method according to embodiments described herein was compared with a method that uses TAR. Electrograms from the CS catheter or pacing catheter were used to obtain TAR when required. A bank of CFs including polynomial functions (up to $3^{rd}$ order polynomial) and also Gaussian RBF centered around the recording electrodes was used.

7.1 Collision During Pacing (Advisor™ HD Grid Catheter)

In the first case, an Advisor™ HD Grid (Abbott, St. Paul, MN) catheter was used to map the left atrium of a 63 year old male patient with persistent AF. Sinus rhythm was achieved after pulmonary vein isolation; subsequently, distal electrodes of the ablation and the CS catheters were used for synchronous pacing with a cycle length of 400 ms. During the pacing the Grid catheter with 16 electrodes (inter-electrode spacing of 4 mm) was placed at 12 different left atrium sites. Pacing impulses were used for TARs and the maximum negative slope of the unipolar EGM collected during sequential recording were used to obtain the LATs at the recording sites. The estimated LATs and the locations of the recording electrodes were used to create an isochronal activation map as shown in FIG. 5A. In this figure the electrodes are shown with circles, where the electrodes during each sequential recording are presented with a similar marker, and the pacing electrodes of the CS and ablation catheters are marked with arrows. FIG. 5B shows the isochronal propagation map of the gold standard approach with the TAR. A total of C=50 terms were used to expand the ATF. The relative LS error between the measured LATs and that obtained from estimated ATF is $\|LAT(P)-\hat{T}_{TAR}(P)\|^2/\|LAT(P)\|^2=1\%$. FIG. 5C shows the isochronal propagation map when the TAR is not available. For this case, the relative LS error is $\|LAT(P)-\hat{T}_{noTAR}(P)\|^2/\|LAT(P)\|^2=2.6\%$. FIGS. 6A and 6B show the estimated velocity vector directions on the map, with the TAR and without the TAR, respectively.

7.2 Single and Double Pacing Sites (Reflexion™ HD Catheter)

In a second clinical case (a 60 year old male with paroxysmal AF), propagation mapping was studied after sinus rhythm was achieved. Mapping was done during pacing from CS alone and also during simultaneous pacing from the CS and ablation catheters. During the pacing a Reflexion™ HD catheter (St. Jude Medical, MN, USA) with 20 electrodes (inter-electrode spacing of 2-7-2 mm) was placed at different left atrium sites.

Figures 7A, 7B:
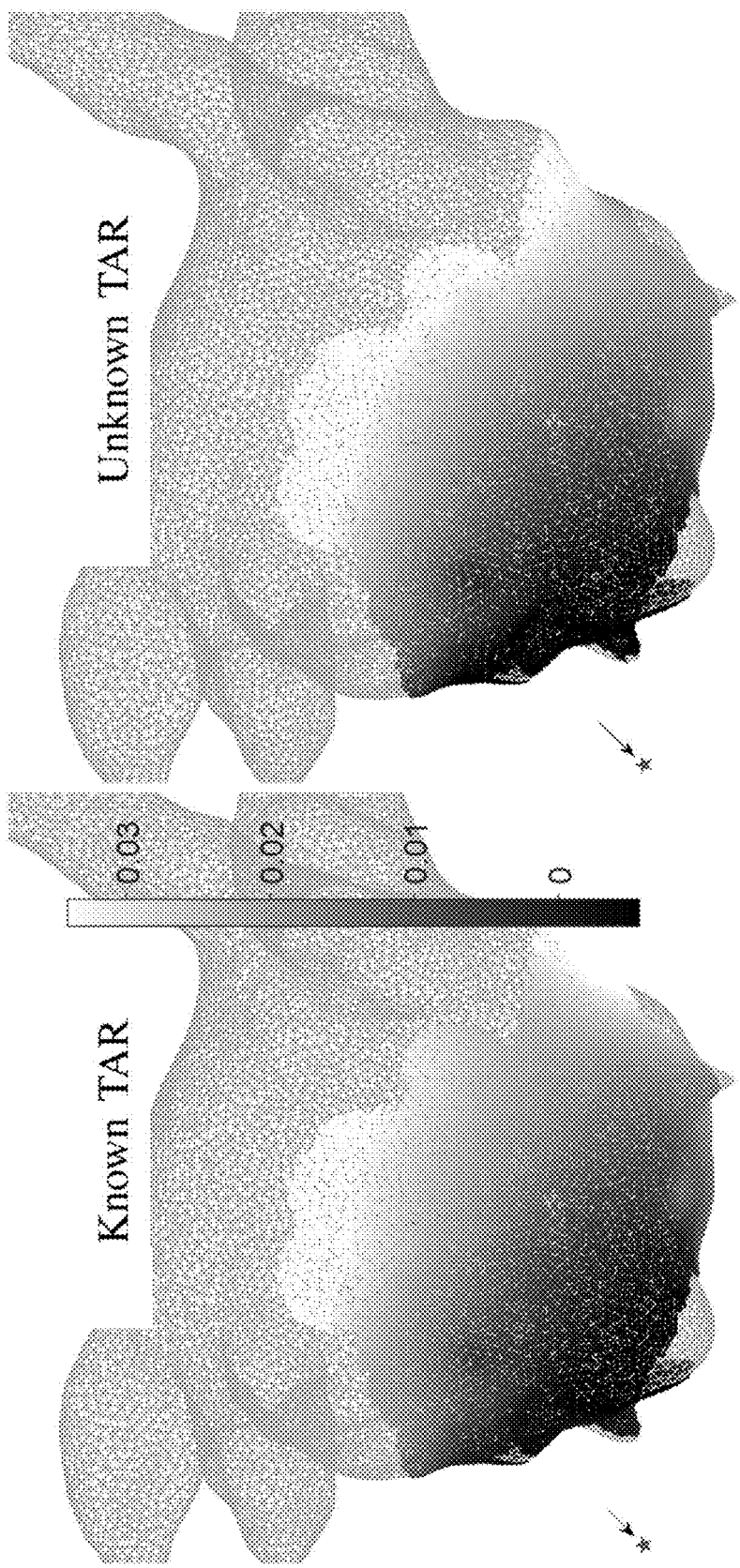
FIGS. 7A and 7B show isochronal propagation maps using a Reflexion™ HD catheter when pacing was done using the CS catheter (marked with an arrow), when the TAR was used and when it was not available, respectively, according to a second example.

FIG. 7A shows the isochronal propagation map when the pacing was done using a CS distal electrode (marked with an arrow) and the pacing signal was also used as a TAR. The relative LS error between the measured LATs and that obtained from estimated ATF was $\|LAT(P)-\hat{T}_{TAR}(P)\|^2/\|LAT(P)\|^2=0.4\%$. FIG. 7B shows the isochronal propagation map when the TAR was not available ($\|LAT(P)-\hat{T}_{noTAR}(P)\|^2/\|LAT(P)\|^2=0.9\%$).

FIG. 8A shows the isochronal propagation map when pacing impulses with a cycle length of 400 ms were generated simultaneously using the distal electrodes of both CS and the ablation catheters (marked with arrows; the CS pacing electrode shown with pentagram on the left); the pacing signal was also used as a TAR and the relative LS error in this case was $\|LAT(P)-\hat{T}_{TAR}(P)\|^2/\|LAT(P)\|^2=0.8\%$. FIG. 8B shows the isochronal propagation map when the TAR was not available and in this case the relative LS error increased to $\|LAT(P)-\hat{T}_{noTAR}(P)\|^2/\|LAT(P)\|^2=2.3\%$.

7.3 Collision During Pacing (Reflexion™ HD Catheter)

In a third clinical case, propagation map generation was studied in a patient (male, 64 years old) with paroxysmal AF after sinus rhythm was achieved. Similar to the previous examples, mapping was done during pacing from two sites. A Reflexion™ HD (St. Jude Medical) catheter was used for mapping.

FIG. 9A shows an isochronal propagation map when pacing impulses with a cycle length of 400 ms were generated simultaneously using the distal electrodes of both CS and ablation catheters (marked with arrows; the CS pacing electrode shown with pentagram on the left). The pacing signal was also used as a TAR and the relative LS error in this case was $\|LAT(P)-\hat{T}_{TAR}(P)\|^2/\|LAT(P)\|^2=0.4\%$. FIG. 9B shows an isochronal propagation map when the TAR was not available and in this case the relative LS error increased to $\|LAT(P)-\hat{T}_{noTAR}(P)\|^2/\|LAT(P)\|^2=0.9\%$. C=60 terms.

Figure 10:
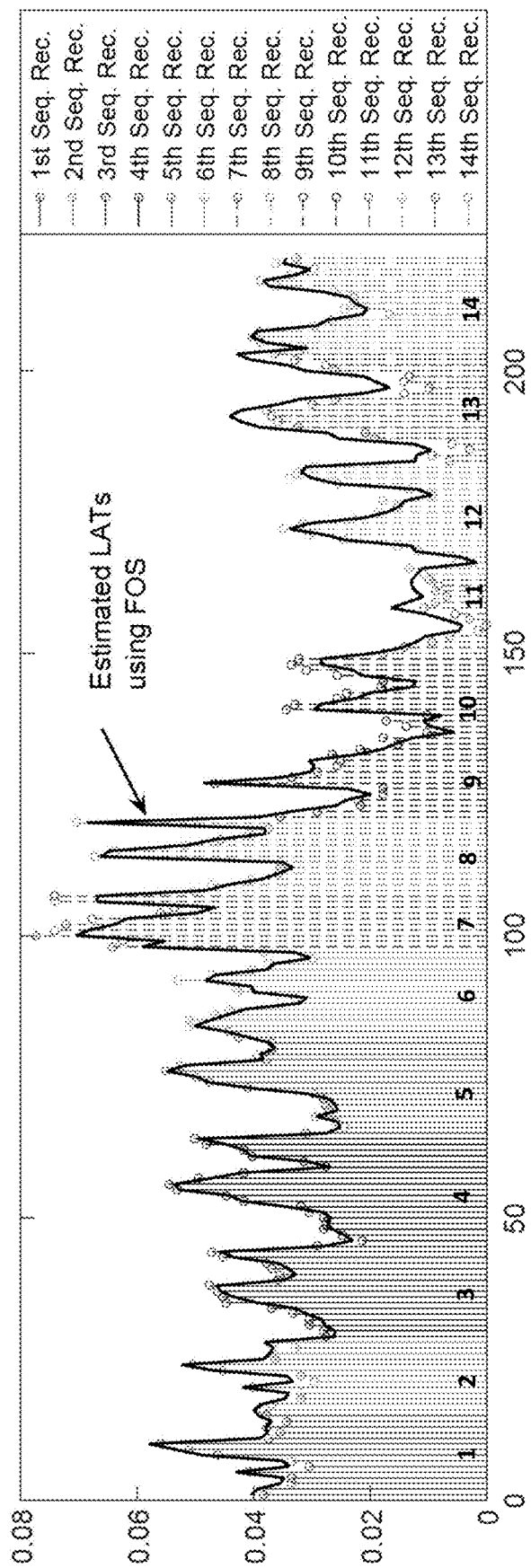
FIG. 10 is a plot showing measured LATs (considering TAR) and estimated LAT values using an embodiment as described herein, wherein a catheter was placed at 14 sites and LATs obtained during each placement are grouped according to the shaded areas.

FIG. 10 shows measured LATs (considering TAR) and estimated values obtained using an embodiment as described herein. A catheter was placed at 14 sites and LATs obtained during each placement are grouped according to the shaded areas. Results show that the relative estimation error according to the embodiment is less than 1%, confirming results reported above.

7.4 Atypical Atrial Flutter

In this example, a propagation map during atrial flutter is produced without using a reference catheter. Unlike the previous examples, here, a larger area (left atrium) was mapped and a large number of points were collected during mapping. In this case where the number of available points is large, the computation complexity of the increases to the point where it might restrict the clinical application of such an embodiment. Therefore, a computationally efficient approach is employed, which can be used to quickly create a map even when there is a large number of points.

In the previous examples, FOS was used for the ATF estimation, in which, in each iteration, the best CF (that minimizes the LS error) was chosen from a bank of CFs and added to the previously selected CFs. Consequently, the computational complexity of FOS increases as the number of elements in the bank of CFs increases. To reduce the computational burden of selecting C CFs and generating the propagation map, instead of adding a single CF in each iteration, we select most of CFs (e.g., 0.9 C) at once. The map may be modified by adding new CFs using FOS. For example, after creating a bank of CFs, a low resolution propagation map is created by using a small number of CFs (e.g., 0.1 C) in the ATF. The time alignment shifts are extracted using the low resolution map. The final propagation map is generated by including a larger number of CFs in the ATF. The following steps describe the computationally efficient selection method (CESM) approach for producing a propagation map in the absence of a TAR.

Create a bank of CFs which contains RBFs (e.g., Gaussian RBF) centered around electrodes locations.

Select $C_1$ CFs, i.e., $\Phi_1, \ldots, \Phi_{C_1}$, that are RBFs centered around the closest electrodes to the $C_1$ uniformly distributed points on the mapped region. For example, in one embodiment the k-means clustering approach may be used to cluster recording points into $C_1$ clusters and the center of the clusters used to obtain uniformly distributed points on the shell. Find the unknown parameters $\{\alpha_i\}_{i=1}^{C_1}$ and $\{t_{1,s}\}_{s=2}^{S}$ by solving the following linear LS problem $$\min_{\{\alpha_i\}_{i=1}^{C_1},\{t_{1,s}\}_{s=2}^{S}} \left\| LAT(P) - \sum_{i=1}^{C_1} \alpha_i \Phi_i(P) - \sum_{s=2}^{S} t_{1,s} q_s \right\|^2. \qquad (10)$$

Remove the estimated time shifts from the LAT of the observation points to obtain $$\widetilde{LAT}(P) = LAT(P) - \Sigma_{s=2}^{S} t_{1,s} q_s.$$

Select $C_2$ CFs $\{\Phi_i\}_{i=1}^{C_2}$ that are RBFs centered around the closest electrodes to the $C_2$ uniformly distributed points on the mapped region. For example, $C_2$ may be significantly larger than $C_1$. Find $\{\alpha_i\}_{i=1}^{C_2}$ and consequently ATF, $\hat{T} = \Sigma_{i=1}^{C_2} \alpha_i \Phi_i(P)$, by solving the following linear LS problem $$\min_{\{\alpha_i\}_{i=1}^{C_2}} \left\| \widetilde{LAT}(P) - \sum_{i=1}^{C_2} \alpha_i \Phi_i(P) \right\|^2. \tag{11}$$

Figure 11A:
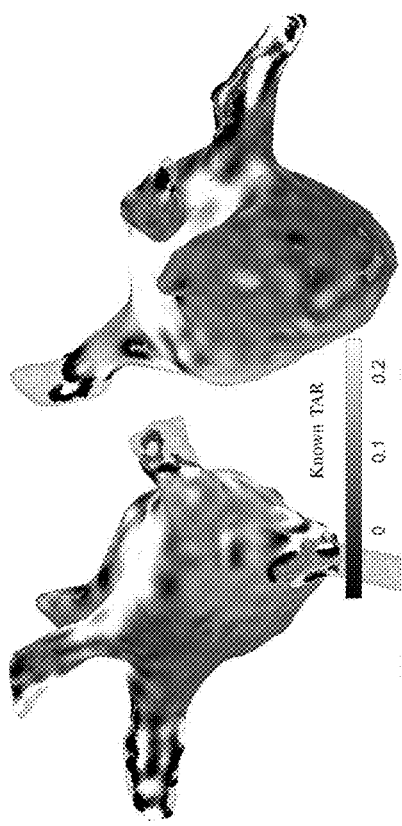
FIGS. 11A and 11B show isochronal propagation maps during atrial flutter in the presence and absence of a TAR, respectively.
Figure 11B:
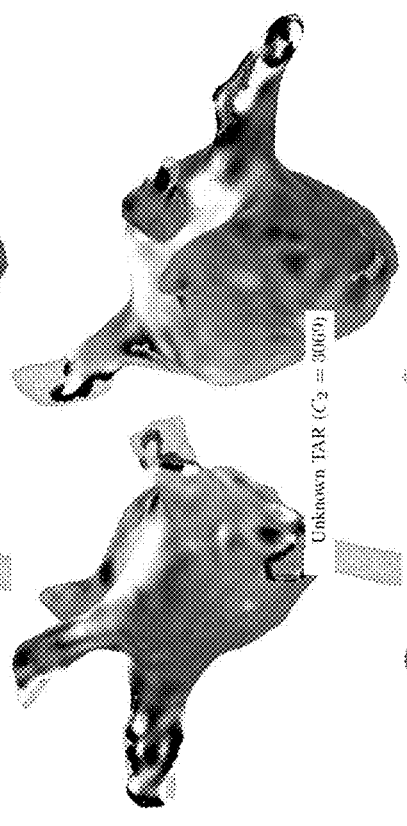
Figure 11C:
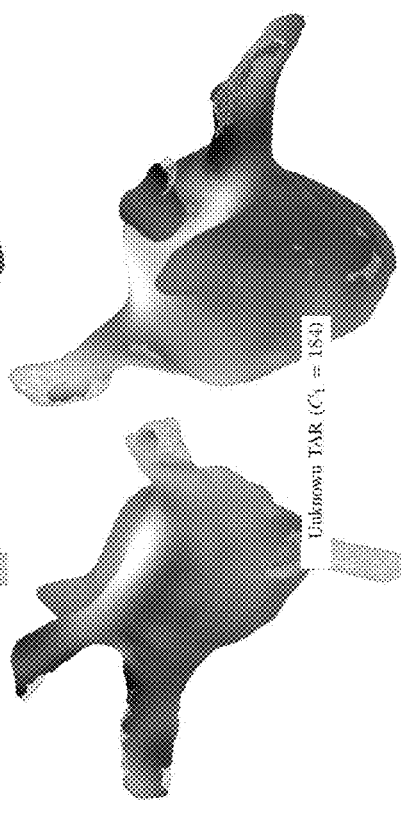
FIG. 11C shows an estimated low resolution propagation map generated according to an embodiment described herein, used to estimate time alignment references.

To demonstrate this embodiment, a sample propagation map was generated. The left atrium of a patient (male, 74 years old) was mapped during an atypical left atrial flutter using an Advisor™ HD catheter. The HD grid mapping catheter was placed at N=691 locations where at each site an average of 5.3±2.1 electrodes were in contact with the tissue (placement with less than 3 electrodes with tissue contact were removed from processing). Consequently, 3683 points with known location coordinates and LATs were collected during the mapping. The above computationally-efficient method with $C_1=184$, $C_2=3069$ was used to estimate ATF. FIGS. 11A and 11B show the isochronal propagation map during atrial flutter in the presence and absence of a TAR, respectively. FIG. 11C shows the estimated 'low resolution' propagation map used to estimate time alignment references. This figure confirms that the embodiment can generate propagation maps which are very similar to the one that uses a TAR in a complex arrhythmia.

7.5 Atrial Fibrillation

As the above clinical examples confirm, the embodiments provide propagation information during the existence of multiple wavefronts and in the absence of any TAR. Therefore, embodiments may be used during complex arrhythmias such as AF in which multiple simultaneous wavefronts exist and TAR is not available.

One way to create a propagation map during AF is to find the most common stable wavefront pattern at each site and then use an embodiment as described herein to combine the stable patterns at different recording locations to generate a propagation map. For this, the LATs and the most stable wavefront at each site are identified. Sites with indiscernible active intervals and unstable wavefronts are removed from the mapping region. After finding the most frequent and stable wavefronts during different catheter placements, an embodiment is used to generate a propagation map. In the following, further details of the aforementioned steps are provided.

Figure 12A:
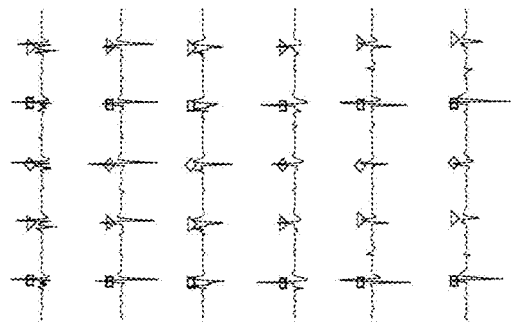
FIGS. 12A-12D show sample electrograms collected during atrial fibrillation from four different sites, wherein the LATs of different wavefronts are identified and wavefronts in each group have the same marker; the time scale in FIG. 12A is different from the time scale in FIGS. 12B-12D.
Figure 12B:
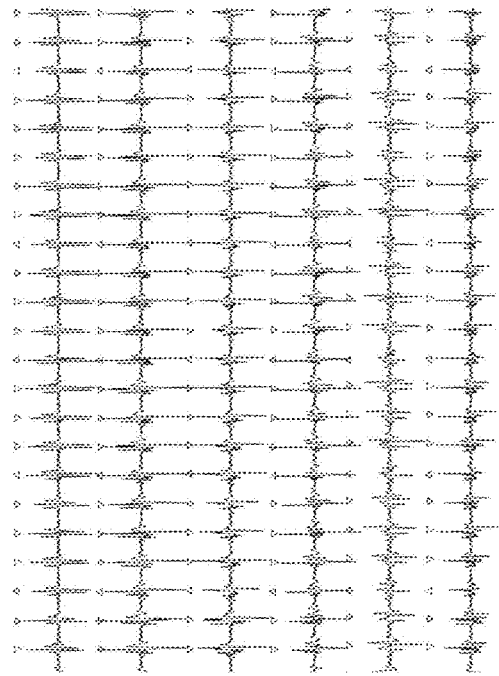
Figure 12C:
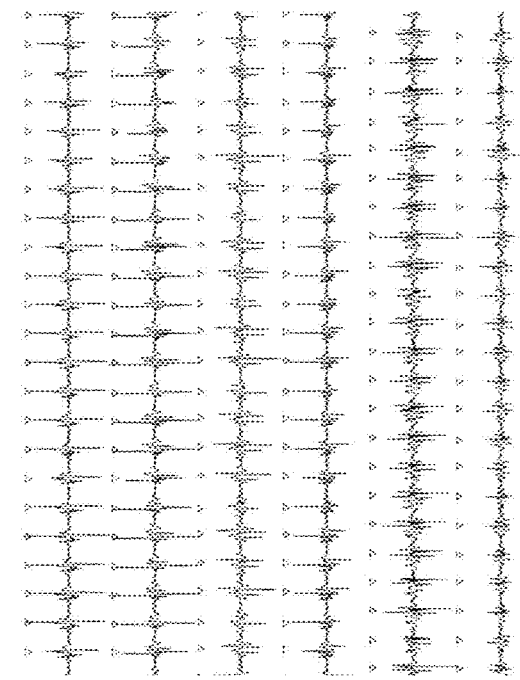
Figure 12D:
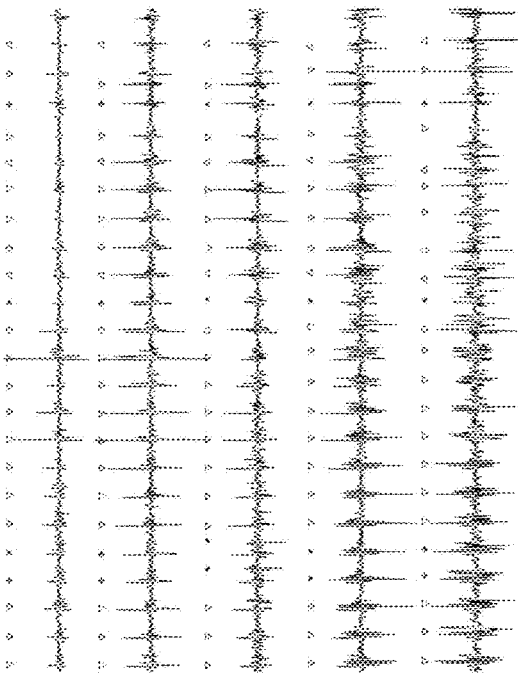

First, the LATs of the collected electrograms are detected and wavefronts are identified [22, 23]. Next, if the correlation coefficient between wavefront patterns is more than a threshold (e.g., 80%) those wavefronts are clustered in a same group. At each site, the group with the largest number of members is identified and the most stable/frequent wavefront patterns are found. Other approaches may also be used to identify stable patterns, e.g., [24]. FIGS. 12A-12D show samples of collected electrograms from four different sites, wherein the LATs of different wavefronts are identified and wavefronts in each group have similar markers. FIG. 12A shows five identified wavefronts (the time scale in this figure is different from the others). Sites with complex long fractionated electrograms without discernible wavefronts and also sites with several equally likely most common patterns are excluded from the analysis (see the second half of FIG. 12D). Finally, a representative of the most stable wavefront pattern at the desired recording sites is used to generate a propagation map.

Figure 13B:
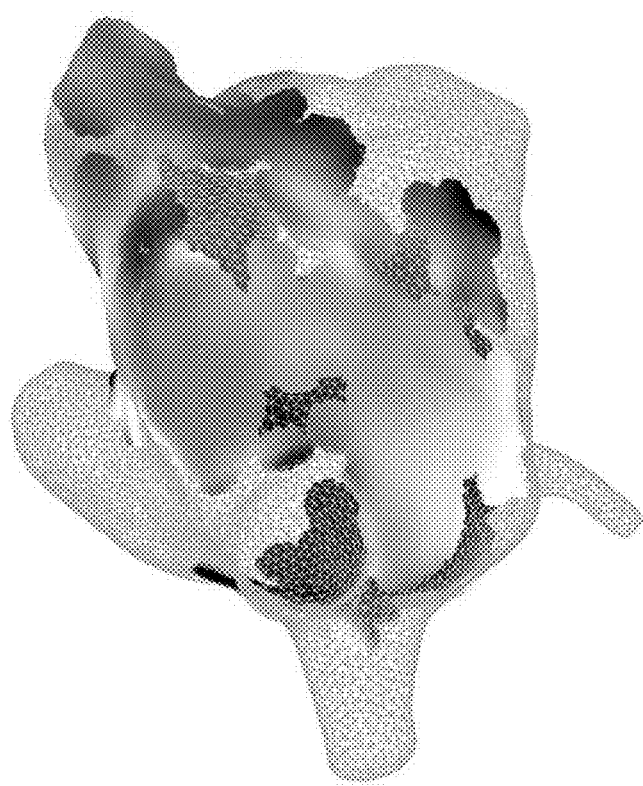
FIGS. 13A and 13B show isochronal maps of stable wavefronts generated from electrograms collected during atrial fibrillation, without a time alignment reference.
Figure 13A:
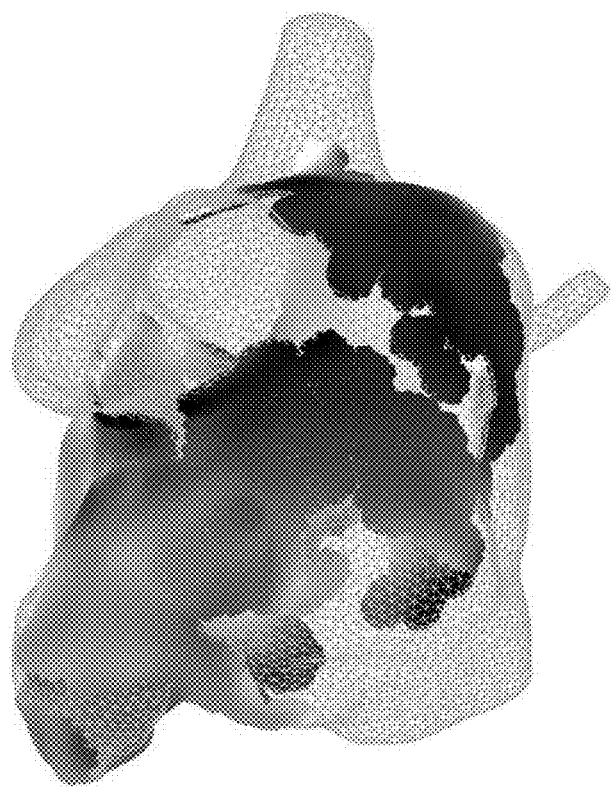

In another clinical example, the left atrium of a patient (male, 69 years old) was mapped during AF. An Advisor™ HD grid mapping catheter was placed in 204 locations and 8-second electrograms were collected; 54 of those recording sites were excluded from this study either because of complex long fractionated electrograms without discernible wavefronts or because the collected points were far from the other recordings. Final N=150 catheter placements had on average 5.2±2.3 electrodes in contact with the tissue (placement with less than 3 electrodes with tissue contact were removed from processing). Electrogram activation time and wavefronts were identified and the most stable wavefront patterns at each location extracted. As a result, 781 points with known location coordinates and LATs were used in the method described above in Section 4.2.4 with $C_1=78$, $C_2=223$ to generate a propagation map. FIGS. 13A and 13B show isochronal maps of stable wavefronts during AF.

Note that above, a propagation map of the most stable/frequent wavefront patterns was generated. If more than one stable wavefront is probable at a site, the one that is stable and most consistent with the wavefronts in the nearby catheters can be identified and used. For example, to select a wavefront in a site with multiple probable/frequent wavefront patterns, first, an ATF based on the most stable wavefront in the adjacent catheter placements can be estimated. Then, among all the probable/possible wavefronts, the one that is most consistent with the estimated ATF is selected. Alternatively, a wavefront is selected that is most consistent with all the nearby recordings instead of the most stable one.

All cited publications are incorporated herein by reference in their entirety.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

REFERENCES

[1] C. Cantwell, C. Roney, F. Ng, J. Siggers, S. Sherwin, and N. Peters, "Techniques for automated local activation time annotation and conduction velocity estimation in cardiac mapping" *Computers in biology and medicine*, vol. 65, no. 4, pp. 229-242, 2015.

[2] M. Masé and F. Ravelli, "Automatic reconstruction of activation and velocity maps from electro-anatomic data by radial basis functions" in *IEEE International Conference of the Engineering in Medicine and Biology Society (EMBC)*. 1 em plus 0.5 em minus 0.4 em IEEE, 2010, pp. 2608-2611.

[3] P. V. Bayly, B. H. KenKnight, J. M. Rogers, R. E. Hillsley, R. E. Ideker, and W. M. Smith, "Estimation of conduction velocity vector fields from epicardial mapping data" *IEEE Transactions on Biomedical Engineering*, vol. 45, no. 5, pp. 563-571, 1998.

[4] A. R. Barnette, P. V. Bayly, S. Zhang, G. P. Walcott, R. E. Ideker, and W. M. Smith, "Estimation of 3-D conduction velocity vector fields from cardiac mapping data," *IEEE Transactions on Biomedical Engineering*, vol. 47, no. 8, pp. 1027-1035, 2000.

[5] R. Dubois, S. Labarthe, Y. Coudiere, M. Hocini, and M. Haissaguerre, "Global and directional activation maps for cardiac mapping in electrophysiology" in *Computing in Cardiology (CinC)*, 2012.

[6] P. Kojodjojo, P. Kanagaratnam, V. Markides, D. Davies, and N. Peters, "Age-related changes in human left and right atrial conduction" *Journal of cardiovascular electrophysiology*, vol. 17, no. 2, pp. 120-127, 2006.

[7] M. H. Shariat, S. Gazor, and D. P. Redfearn, "Cardiac conduction velocity estimation from sequential mapping assuming known Gaussian distribution for activation time estimation error" in *IEEE 38th Annual International Conference of the Engineering in Medicine and Biology Society (EMBC)*. 1 em plus 0.5 em minus 0.4 em IEEE, 2016, pp. 505-508.

[8] M. H. Shariat, S. Gazor, and D. P. Redfearn, "Maximum likelihood cardiac conduction velocity estimation from sequential mapping in the presence of activation time noise with unknown variances" in *IEEE 38th Annual International Conference of the Engineering in Medicine and Biology Society (EMBC)*. 1 em plus 0.5 em minus 0.4 em IEEE, 2016, pp. 2745-2748.

[9] M. H. Shariat, S. Gazor, and D. P. Redfearn, "Maximum likelihood cardiac conduction velocity estimation in the presence of ambiguities in the locations and activation times of the recording points" in *IEEE Canadian Conference on Electrical and Computer Engineering (CCECE)*. 1 em plus 0.5 em minus 0.4 em IEEE, 2016, pp. 1-4.

[10] M. H. Shariat, "Processing the intracardiac electrogram for atrial fibrillation ablation" Ph.D. dissertation, Queen's University (Canada), 2016.

[11] M. Mongillo, "Choosing basis functions and shape parameters for radial basis function methods" *SIAM Undergraduate Research Online*, vol. 4, pp. 190-209, 2011.

[12] D. Lowe and D. Broomhead, "Multivariable functional interpolation and adaptive networks" *Complex systems*, vol. 2, no. 3, pp. 321-355, 1988.

[13] D. S. Broomhead and D. Lowe, "Radial basis functions, multi-variable functional interpolation and adaptive networks" Royal Signals and Radar Establishment Malvern (United Kingdom), Tech. Rep., 1988.

[14] M. J. Korenberg and L. D. Paarmann, "Applications of fast orthogonal search: Time-series analysis and resolution of signals in noise" *Annals of biomedical engineering*, vol. 17, no. 3, pp. 219-231, 1989.

[15] R. Tibshirani, "Regression shrinkage and selection via the LASSO" *Journal of the Royal Statistical Society. Series B (Methodological)*, pp. 267-288, 1996.

[16] S. Chen, C. F. Cowan, and P. M. Grant, "Orthogonal least squares learning algorithm for radial basis function networks" *IEEE Transactions on neural networks*, vol. 2, no. 2, pp. 302-309, 1991.

[17] A. El-Shafie, A. Noureldin, D. McGaughey, and A. Hussain, "Fast orthogonal search (FOS) versus fast fourier transform (fft) as spectral model estimations techniques applied for structural health monitoring (SHM)" *Structural and Multidisciplinary Optimization*, vol. 45, no. 4, pp. 503-513, 2012.

[18] J. M. Rogers and A. D. McCulloch, "A collocation-galerkin finite element model of cardiac action potential propagation" *IEEE Transactions on Biomedical Engineering*, vol. 41, no. 8, pp. 743-757, 1994.

[19] J. W. Thomas, *Numerical partial differential equations: finite difference methods*. 1 em plus 0.5 em minus 0.4 em Springer Science & Business Media, 2013, vol. 22.

[20] A. M. Pertsov, J. M. Davidenko, R. Salomonsz, W. T. Baxter, and J. Jalife, "Spiral waves of excitation underlie reentrant activity in isolated cardiac muscle" *Circulation research*, vol. 72, no. 3, pp. 631-650, 1993.

[21] V. Jacquemet, N. Virag, Z. Ihara, L. Dang, O. Blanc, S. Zozor, J. VESIN, L. Kappenberger, and C. Henriquez, "Study of unipolar electrogram morphology in a computer model of atrial fibrillation" *Journal of cardiovascular electrophysiology*, vol. 14, no. s10, 2003.

[22] M. H. Shariat, S. Gazor, and D. P. Redfearn, "Bipolar intracardiac electrogram active interval extraction during atrial fibrillation" *IEEE Transactions on Biomedical Engineering*, vol. 64, no. 9, pp. 2122-2133, 2017.

[23] M. H. Shariat, J. Hashemi, S. Gazor, and D. P. Redfearn, "Activation detection of intracardiac electrogram during atrial fibrillation based on the variance equality test" in *IEEE 28th Canadian Conference on Electrical and Computer Engineering (CCECE)*, 2015, pp. 387-391.

[24] P. Kuklik, B. Schäffer, R. Ö. Akbulak, M. Jularic, C. Jungen, J. Nuehrich, N. Klatt, C. Eickholt, C. Meyer, and S. Willems, "Stability of conduction patterns in persistent atrial fibrillation" *Computing*, vol. 44, p. 1, 2017.

The invention claimed is:

1. A method for generating a map for cardiac wavefront propagation and for treating atrial arrhythmia, comprising:
   obtaining a set of local activation times (LATs) of electrograms and location coordinates of electrodes of a catheter;
   using a processor to execute code stored on non-transitory storage media compatible with the processor, the code containing instructions to direct the processor to generate an activation time function (ATF) by:
   using two or more candidate functions (CFs) selected from a bank of CFs and estimating weighting and unknown parameters of the CFs to match available LATs of the electrodes;
   determining the ATF as a combination of the selected CFs that matches the LATs;
   using the ATF to generate at least one map selected from a propagation map, an isochronal map, and a conduction velocity map of the cardiac wavefront propagation; and
   treating atrial arrhythmia in a subject by performing ablation therapy guided by the at least one map.

2. The method of claim 1, wherein the generating the activation time function and the at least one map does not require using a reference catheter for time alignment.

3. The method of claim 1, wherein the ATF is a weighted summation of nonlinear, nonorthogonal, candidate functions (CFs) of coordinates of the electrodes of the catheter.

4. The method of claim 1, comprising using a method selected from exhaustive search, FOS, LASSO, and OLS to expand the activation time function as a linear combination of CFs.

5. The method of claim 1, comprising using a computationally efficient selection method (CESM) for selecting CFs; and
   modifying the ATF by selecting additional CFs.

6. The method of claim 5, wherein the at least one map is a low resolution map created by using a small number of CFs in the ATF;
   extracting time alignment shifts using the low resolution map; and generating a final propagation map by including a larger number of CFs in the ATF.

7. The method of claim 1, comprising using the activation times to estimate the conduction velocity.

8. The method of claim 1, comprising using an absolute error of the LATs and an activation map at different electrode placements to create an error map;
    wherein the error map shows reliability of the generated at least one map and identifies sites with complex signals and/or sites with low density of collected electrogram signals.

9. The method of claim 1, wherein the set electrograms is obtained simultaneously from a single catheter placement.

10. The method of claim 1, wherein the set of electrograms is obtained from two or more catheter placements during sequential recording, with unknown time shifts between different recording placements.

11. The method of claim 10, comprising including a predefined binary level set of CFs in the output of the selected CFs;
    obtaining a constant value time shift of the activation times of the recordings; and
    identifying sequential time alignment references (TARs);
    wherein phase differences between sequential recording at different sites are compensated, and the sequential recording is transformed to continuous recording.

12. The method of claim 11, comprising using the selected CFs with a method selected from FOS, LASSO, OLS, and CESM to identify the sequential TARs.

13. The method of claim 1, wherein the atrial arrhythmia comprises at least one of atrial flutter, atrial fibrillation, and atrial tachycardia.

14. The method of claim 1, wherein the atrial arrhythmia comprises atrial fibrillation.

15. The method of claim 1, wherein a CESM is used to output the at least one map; wherein the CESM comprises selecting all or a portion of the CFs at once.

16. The method of claim 15, wherein the CESM comprises selecting radial basis CFs with centres uniformly distributed on a mapping region.

17. The method of claim 1, comprising dividing available measurement points with known LATs into clusters and selecting CFs to generate an ATF for each cluster; and
    generating the at least one map using an ATF that uses the selected CFs of each cluster; or
    generating the at least one map using an ATF that uses the selected CFs of each cluster and one or more additional CFs selected from previously non-selected CFs.

18. The method of claim 1, comprising producing a reliability map based on an error between measured LATs and LATs obtained with the determined ATF;
    wherein the reliability map shows one or more of: sites where the determined ATF properly describes the wavefront propagation; sites where the determined ATF is unable to predict activation time and complexity of the wavefront propagation.

* * * * *